(12) United States Patent
Ding et al.

(10) Patent No.: US 10,975,006 B2
(45) Date of Patent: Apr. 13, 2021

(54) INTEGRATED PROCESSES FOR PARA-XYLENE PRODUCTION

(71) Applicants: SCG Chemicals Company Limited, Bangkok (TH); Sulzer Management AG, Winterthur (CH)

(72) Inventors: Zhongyi Ding, Katy, TX (US); Sachin Joshi, Katy, TX (US); Weihua Jin, Katy, TX (US)

(73) Assignees: SCG Chemicals Co., Ltd., Bangkok (TH); Sulzer Management AG, Winterthur (CH)

( * ) Notice: Subject to any disclaimer, the term of this patent is extended or adjusted under 35 U.S.C. 154(b) by 0 days.

(21) Appl. No.: 16/516,687

(22) Filed: Jul. 19, 2019

(65) Prior Publication Data

US 2020/0024216 A1    Jan. 23, 2020

Related U.S. Application Data

(60) Provisional application No. 62/701,085, filed on Jul. 20, 2018.

(51) Int. Cl.
| | |
|---|---|
| *C07C 5/27* | (2006.01) |
| *C07C 7/08* | (2006.01) |
| *C07C 7/14* | (2006.01) |
| *C07C 7/12* | (2006.01) |
| *C07C 7/00* | (2006.01) |

(52) U.S. Cl.
CPC ............ *C07C 7/005* (2013.01); *C07C 5/2702* (2013.01); *C07C 5/277* (2013.01); *C07C 5/2732* (2013.01); *C07C 7/08* (2013.01); *C07C 7/12* (2013.01); *C07C 7/14* (2013.01)

(58) Field of Classification Search
None
See application file for complete search history.

(56) References Cited

U.S. PATENT DOCUMENTS

| | | |
|---|---|---|
| 3,105,017 A | 9/1963 | Amir et al. |
| 3,584,068 A | 6/1971 | Jackson et al. |
| 3,624,172 A | 11/1971 | Adams |

(Continued)

FOREIGN PATENT DOCUMENTS

| | | |
|---|---|---|
| CN | 104387224 A | 3/2015 |
| GB | 1198592 | 7/1970 |

(Continued)

*Primary Examiner* — Philip Y Louie
*Assistant Examiner* — Alyssa L Cepluch
(74) *Attorney, Agent, or Firm* — Banner & Witcoff, Ltd.

(57) ABSTRACT

Para-xylene production processes are disclosed, with such processes being integrated with extractive distillation or other separation to effectively separate, for example to remove and recover, ethylbenzene and other components that co-boil with the isomers of xylene. This allows for xylene isomerization, downstream of the separation of para-xylene from its other isomers, to be operated under milder conditions (e.g., liquid phase, absence of added hydrogen) without the need for ethylbenzene conversion. The associated decreased yields of byproducts such as light gases and non-aromatic hydrocarbons, together with the generation of purified ethylbenzene having value for styrene monomer production, can significantly improve overall process economics.

20 Claims, 5 Drawing Sheets

(56) References Cited

U.S. PATENT DOCUMENTS

| | | | |
|---|---|---|---|
| 3,702,347 A | | 11/1972 | Adams |
| 3,856,871 A | | 12/1974 | Haag et al. |
| 3,856,874 A | | 12/1974 | Hayward |
| 4,101,596 A | | 7/1978 | Mitchell et al. |
| 4,224,141 A | * | 9/1980 | Morrison ................ B01J 29/40 208/134 |
| 4,299,668 A | * | 11/1981 | Berg ........................ C07C 7/08 203/51 |
| 4,435,608 A | | 3/1984 | Koetsier et al. |
| 5,329,061 A | | 7/1994 | Swift |
| 5,397,441 A | | 3/1995 | Berg |
| 5,495,061 A | | 2/1996 | Kulprathinpanja |
| 5,948,950 A | | 9/1999 | Hotier et al. |
| 6,369,287 B1 | | 4/2002 | Magne-Drisch et al. |
| 2002/0082461 A1 | | 6/2002 | Magne-Drisch et al. |
| 2002/0082462 A1 | | 6/2002 | Ferraro et al. |
| 2007/0004948 A1 | | 1/2007 | Bauer |
| 2015/0266794 A1 | * | 9/2015 | Ou .......................... C07C 5/277 585/474 |
| 2016/0272558 A1 | * | 9/2016 | Bender ................ B01J 19/2445 |
| 2017/0247303 A1 | | 8/2017 | Thirasak et al. |

FOREIGN PATENT DOCUMENTS

| | | | | |
|---|---|---|---|---|
| WO | 2015142454 A1 | 9/2015 | | |
| WO | 2016036326 A1 | 3/2016 | | |
| WO | 2016036388 A1 | 3/2016 | | |
| WO | 2016036392 A1 | 3/2016 | | |
| WO | WO-2016036326 A1 | * | 3/2016 | ............... C07C 7/08 |
| WO | 2017105617 A1 | 6/2017 | | |

* cited by examiner

US 10,975,006 B2

INTEGRATED PROCESSES FOR PARA-XYLENE PRODUCTION

CROSS-REFERENCE TO RELATED APPLICATIONS

This application claims priority to U.S. provisional application No. 62/701,085, filed Jul. 20, 2018, which is incorporated by reference in its entirety.

FIELD OF THE INVENTION

The present invention relates to processes for producing para-xylene from an impure ethylbenzene-containing feed that comprises mixed xylene isomers, such as a reformate obtained from naphtha reforming or a pyrolysis gasoline obtained from naphtha cracking. Para-xylene production is integrated with ethylbenzene separation (e.g., via extractive distillation) to recover the ethylbenzene.

BACKGROUND OF THE INVENTION

The isomers of xylene (dimethylbenzene), namely ortho-xylene, meta-xylene, and para-xylene, are important chemical intermediates, with para-xylene having by far the greatest commercial significance. The primary application of para-xylene involves its oxidation to make terephthalic acid. Terephthalic acid, in turn, is used to make polymers such as polytrimethyleneterephthalate (PTT), polybutyleneterephthalate (PBT), and polyethyleneterephthalate (PET). PET, one of the largest volume polymers in the world, is made via condensation polymerization of terephthalic acid with ethylene glycol. Given the large market for PET plastics and fibers, in addition to other end products produced from para-xylene, there is a substantial demand for this intermediate in high purity.

As a source of these xylene isomers, the refinery process known as reforming generally refers to the conversion (or "aromatization") of a naphtha hydrocarbon feed, as a crude oil fraction, to these $C_8$ aromatic hydrocarbons, in addition to benzene and toluene as other significant products. The effluent of the reforming reaction zone or reformer (e.g., a catalytic reformer with continuous or semi-regenerative catalyst regeneration) is separated by distillation and in particular using a reformate splitter. The $C_6$ and $C_7$ aromatic hydrocarbons, namely benzene and toluene, are often recovered in a splitter overhead fraction, whereas the $C_8$ aromatic hydrocarbons, namely the xylene isomers in addition to ethylbenzene, are essentially all recovered in a splitter bottoms fraction at approximately their equilibrium concentrations. Higher-boiling $C_9$ and $C_{10}$ aromatic hydrocarbons contained in this reformate splitter bottoms fraction are conventionally separated by downstream distillation, for example using a xylene splitter or xylene column, from the $C_8$ aromatic hydrocarbons and ethylbenzene in this stream. Similar separations, involving removing lower-boiling $C_6/C_7$ aromatic hydrocarbons and/or higher-boiling $C_9/C_{10}$ aromatic hydrocarbons, can be performed on other known commercial products, such as pyrolysis gasoline obtained from naphtha cracking, to increase the concentrations of mixed xylenes and ethylbenzene in fractions recovered from such products.

The high-value para-xylene can be separated from a stream of mixed xylenes and ethylbenzene, for example obtained as a low-boiling fraction (e.g., overhead fraction) of a xylene column as described above, using a para-xylene separation process. Due to the similar boiling points of the xylene isomers, xylene separation processes are not performed economically using distillation. Such processes instead generally rely on adsorptive separation using a simulated moving bed (SMB) of adsorbent having micropores of the proper size and geometry for selectively adsorbing para-xylene over the other xylene isomers. Representative adsorbents and processes for the selective separation para-xylene in this manner are described, for example, in U.S. Pat. Nos. 5,495,061 and 5,948,950. Alternatively, para-xylene may be separated by selective crystallization due to its higher melting temperature relative to the other xylene isomers, for example according to a process described in U.S. Pat. No. 5,329,061.

Regardless of the particular method used for para-xylene separation and recovery, a resulting para-xylene lean or depleted effluent stream is obtained. In the case of SMB, adsorbent-based separations, this effluent may be referred to as a "raffinate," whereas it is commonly termed a "reject filtrate" in the case of crystallization. Downstream of the xylene separation zone, this para-xylene-depleted effluent, comprising predominantly ortho-xylene and meta-xylene, is typically further processed in an isomerization reaction zone to restore approximately an equilibrium concentration of the xylene isomers, including about 20-25% by weight of para-xylene. The para-xylene produced from this isomerization may advantageously be recycled to the xylene separation zone for its separation and recovery, thereby improving the overall yield of recovery of para-xylene, while recycling the other xylene isomers essentially to extinction. Otherwise, product obtained from the isomerization zone, or "isomerate," may be recycled to the xylene column, such that $C_9$, $C_{10}$, and/or higher molecular weight hydrocarbons (particularly aromatic hydrocarbons), as reaction byproducts, may be continuously removed. In either case, successive zones for para-xylene separation (by selective adsorption or selective crystallization) and isomerization, operating in combination with the recycle of less desirable xylene isomers, are commercially implemented for the recovery of para-xylene from $C_8$ aromatic hydrocarbon products, including those obtained from catalytic reforming, naphtha cracking, and other processes.

An essentially closed loop operation, formed by continuous recycle of the isomerate back to either the para-xylene separation zone and/or upstream xylene column, is generally desirable for maximizing overall product recovery. Nonetheless, this is known to lead to the accumulation of certain components that are continuously fed to this process flow loop, as a result of their boiling points being close to those of the xylene isomers and corresponding difficulty of their removal through conventional, upstream fractionation (e.g., in a reformate splitter or xylene column, described above). One such component is ethylbenzene, which, depending on the catalyst used in the isomerization reaction zone, is isomerized only to a limited extent in the isomerization zone to produce mixed xylenes, from which additional para-xylene may ultimately be produced and separated. Methods for the separation of ethylbenzene through intensive distillation (e.g., using multiple columns) have proven uneconomical.

Alternative solutions for limiting the excessive accumulation of ethylbenzene have therefore targeted the conversion of this component, for example by increasing the extent to which it is isomerized to xylenes and/or dealkylated (or cracked) to benzene and ethylene, which are more easily separable from the process flow loop. Benzene formation is not particularly problematic, as it is nonetheless an aromatic hydrocarbon that can be converted to xylenes through disproportionation and/or transalkylation reactions, which are often incorporated in aromatics processing complexes. However, increases in catalytic functionality toward ethylbenzene conversion in the isomerization zone (either through dealkylation or enhanced isomerization) have invariably led to corresponding increases in non-selective side reactions, resulting in the formation of other byproducts that are less valuable and/or less easily converted to desirable components.

Particular examples of such byproducts are non-aromatic (e.g., paraffinic, cycloparaffinic, and/or naphthenic) hydrocarbons that may, like the ethylbenzene sought to be eliminated, similarly accumulate the process flow loop. Non-aromatic hydrocarbons and other byproducts further contribute to overall losses of product yield and consequently result in less favorable process economics. The same detrimental effects are encountered when conditions in the isomerization zone, as opposed to mere changes in the catalyst formulation (such as increased acidity of the catalyst support to promote cracking), are adjusted to enhance ethylbenzene conversion. That is, the increases in operating severity, as needed to react this component, lead to the formation of non-aromatic hydrocarbons and other byproducts, again with the overall effect of decreasing para-xylene yield. More recently, it has been proposed to add a dehydrogenation reactor downstream of the isomerization reactor, in order to offset at least some of the byproduct formation, by converting naphthenic hydrocarbons back to the more desirable aromatic hydrocarbons.

However, any catalyst formulations and/or process conditions designed to promote reactions other than xylene isomerization, such as the isomerization or dealkylation of ethylbenzene, or otherwise the dehydrogenation of naphthenic hydrocarbons as described above, invariably increase costs and complexity associated with para-xylene production according to conventional technology. Increased isomerization operating severity to convert ethylbenzene can involve the introduction and recycle of hydrogen, leading to significant capital and operating expenses. Moreover, the proposals offered to date do not completely address aromatic ring loss, or formation of non-aromatic hydrocarbons through side reactions, as a consequence of converting ethylbenzene.

In general, the production of para-xylene is practiced commercially in large-scale facilities, with the costs among various producers in the industry being highly competitive. Refining and petrochemical operators must therefore strive continually to achieve the highest possible performance characteristics (e.g., conversion, separation, and recovery) in integrated process units, in the most economically attractive manner (e.g., in terms of capital and operating costs). To this end, a conventional aromatics complex is described in Meyers et al., HANDBOOK OF PETROLEUM REFINING PROCESSES, 4$^{th}$ Edition (2016). There remains a need in the art for para-xylene production from $C_8$ aromatic hydrocarbon-containing products, which offer an efficient solution for the management of ethylbenzene and other components that accumulate in the process flow loop.

SUMMARY

The present invention is associated with the discovery of para-xylene production processes that are integrated with the effective removal and recovery of ethylbenzene and other components that co-boil with the isomers of xylene. These components refer generally to non-xylene hydrocarbons that are generated and/or introduced to the process and that have boiling point temperatures, such that the expense associated with conventional distillation does not justify the value obtained from the separation and recovery of such components from xylene-containing process streams, including those forming a para-xylene process flow loop. Such components may generally have boiling points within 15° C. (+/−15° C. or +/−27° F.), within 10° C. (+/−10° C. or +/−18° F.), or within 5° C. (+/−5° C. or +/−9° F.), of the boiling point of para-xylene (138° C. or 280° F.) and therefore include, in addition to ethylbenzene, $C_8$ paraffinic hydrocarbons (e.g., n-octane and isomers of iso-octane), $C_7$-$C_8$ cycloparaffinic hydrocarbons (e.g., ethylcyclohexane and cyclooctane), $C_9$ naphthenic hydrocarbons (e.g., isomers of trimethylcyclohexane) and other non-aromatic compounds.

Absent their separation and recovery, for example using extractive distillation as described herein, these components must be converted to products (e.g., benzene and ethylene in the case of ethylbenzene cracking) that can ultimately form para-xylene (e.g., by transalkylation) or otherwise products that can be removed elsewhere in the para-xylene production process. For example, $C_{12}$ hydrocarbons, formed as a byproduct of various reactions, such as ethylbenzene cracking, may be removed in a $C_9^+$ hydrocarbon stream, as a high boiling fraction obtained from separation in a xylene column. As described above, conventional para-xylene production processes have relied upon the conversion of co-boiling components to avoid their excessive accumulation in the para-xylene process flow loop. The modification of isomerization catalysts and/or isomerization operating conditions to target such conversion (e.g., ethylbenzene isomerization, ethylbenzene cracking, and/or naphthenic hydrocarbon dehydrogenation), has led to non-selective side reactions that ultimately reduce para-xylene production efficiency.

In contrast, the present invention is associated with the discovery of para-xylene production processes in which ethylbenzene and other components that co-boil with the isomers of xylene can be recovered as products, without significant conversion. Advantageously, the isomerization zone (e.g., conditions in an isomerization reactor and/or an isomerization catalyst used in this reactor) can be dedicated essentially or completely to ortho-xylene and meta-xylene isomerization to para-xylene. According to some embodiments, this can require less severe and/or less complex operating parameters, such as liquid-phase (as opposed to vapor-phase) operation in the isomerization zone (or isomerization reactor in this zone), without the need for hydrogen introduction and its associated recycle, consumption (e.g., in the ethylbenzene cracking reaction), and inevitable losses (e.g., gaseous purge stream losses and/or liquid stream solution losses).

In addition to reduced hydrogen consumption relative to conventional para-xylene production processes, the recovery of ethylbenzene according to processes described herein can provide further economic benefits in terms of reduced yields of byproducts, and particularly those generated in conventional isomerization in which ethylbenzene conversion functionality is characteristic of the isomerization catalyst and/or process conditions used. Such byproducts include non-aromatic hydrocarbons, associated with aromatic ring loss reactions, as well as light hydrocarbon gases (e.g., ethylene), associated with cracking reactions. Accordingly, processes described herein can incorporate an ethylbenzene (EB) separation unit (e.g., comprising extractive distillation) for the recovery of ethylbenzene, thereby improving the yield of liquid products, including, for example, an ethylbenzene-rich product having economic value for downstream styrene monomer production. Moreover, as a result of relaxing or eliminating the requirement for ethylbenzene conversion in the isomerization zone, including the avoidance of introducing hydrogen for ethylbenzene cracking, the yield of low-value gaseous products (e.g., hydrogen-containing purge streams that include byproduct ethylene) may be significantly reduced. Overall utility (e.g., hydrogen recycle compressor) costs can also be reduced.

Those skilled in the art will appreciate that even modest improvements in any of the above parameters, such as reductions in hydrogen consumption, byproduct yields, and/or utility requirements, as well as increases in para-xylene yield and/or overall product value (e.g., due to the generation of an ethylbenzene-rich product), can impart significant economic advantages.

These and other embodiments and aspects relating to the present invention are apparent from the following Detailed Description.

Figure 1:
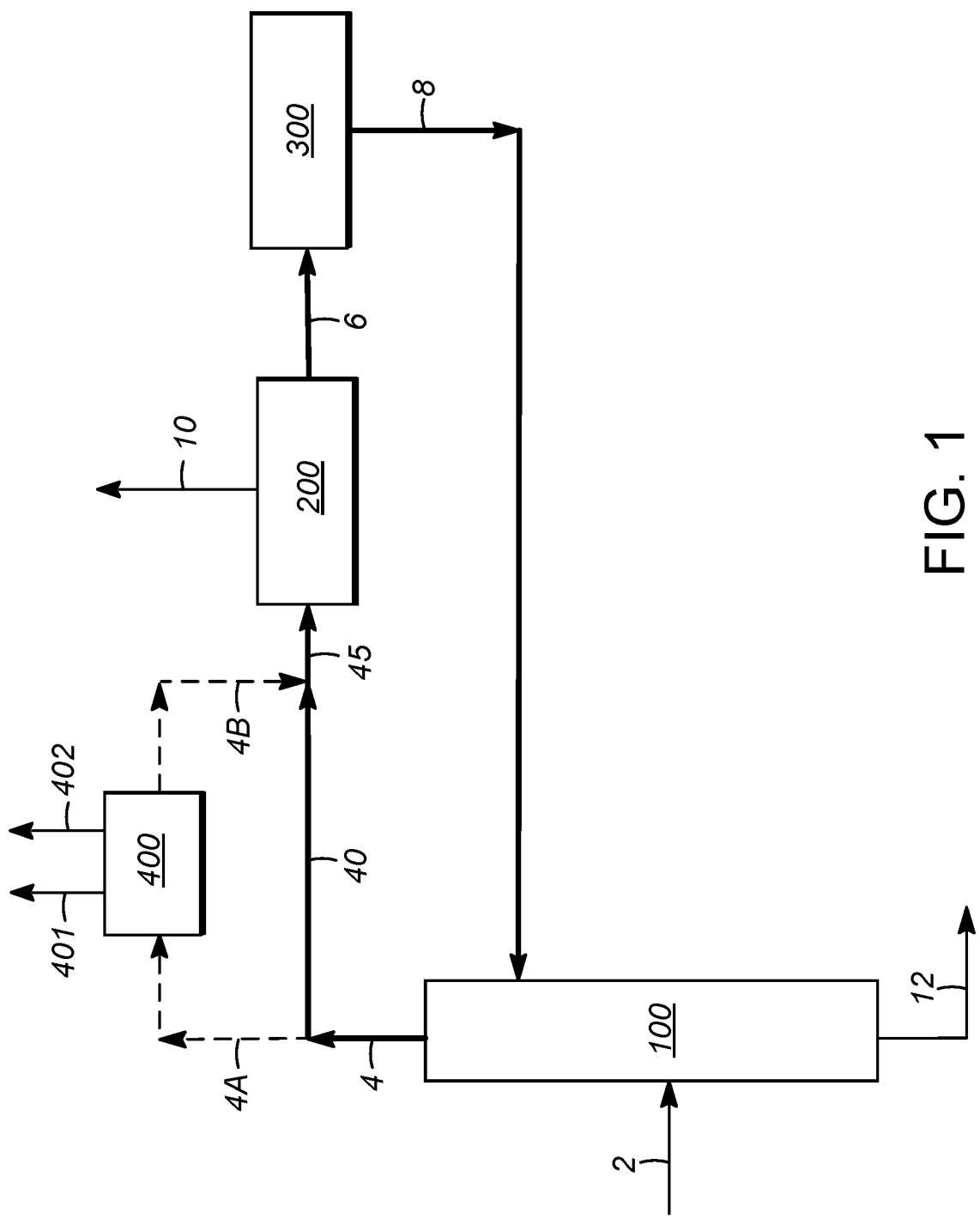
FIGS. 1-4 depict representative processes for the recovery of para-xylene, for example from an impure ethylbenzene-containing feed, in which an ethylbenzene (EB) separation unit is used at various alternative points in process, to prevent the excess accumulation of ethylbenzene in process streams.

The features referred to in the FIGS. 1-5 are not necessarily drawn to scale and should be understood to present a schematic illustration of representative embodiments of the invention and/or principles involved. To aid in understanding, equipment such as reactors and other vessels, valves, pumps, compressors, heat exchangers, instrumentation, and auxiliary process flow streams, all of which would be apparent to those skilled in the art with knowledge of the present specification, are not shown. Processes according to other embodiments of the invention will have configurations, components, and operating parameters determined, in part, by their intended application and the environment in which they are used.

DETAILED DESCRIPTION

General Terms

Embodiments described herein utilize the separation of ethylbenzene to improve the overall economics of para-xylene production. For this separation, certain embodiments utilize a unit operation for the separation and/or recovery of ethylbenzene and/or other products that improve the overall product stream value obtained from the para-xylene production process, with such unit operation being referred to as an "EB separation unit" that may be utilized at various points in a para-xylene production process. Ethylbenzene separation, for example using an EB removal unit, may be performed, for example, by extraction, distillation, or a combination of both extraction and distillation, which combination is a preferred separation technique that is referred to as extractive distillation and described in more detail below. Distillation, whether used alone or in combination with extraction, can refer to pressurized or vacuum distillation and may include the introduction of an upwardly flowing gas (stripping agent) or a downwardly flowing liquid (solvent), to aid in the desired separation. According to preferred embodiments, an EB removal unit as described herein may comprise extractive distillation, such that a preferred EB removal unit is an extractive distillation zone.

As described herein, steps such as "separating," "isomerizing," "recycling," "removing," (e.g., by extractive distillation), may be described in terms of being performed on "at least a portion" of a designated process stream (e.g., an impure ethylbenzene-containing feed, a $C_8$ aromatic hydrocarbon stream, a para-xylene-depleted effluent, or a xylene-equilibrated isomerate). The step may therefore be performed on the entire stream, substantially all (e.g., at least about 95%) of the stream, or some other fraction (e.g., at least about 50%) of the stream. The phrase "at least a portion" is therefore meant to emphasize the possibility of intervening separations (e.g., distillation) that may be used to remove some fraction (e.g., enriched in an impurity such as $C_7^-$ hydrocarbons) of the designated process stream. In addition, this phrase accounts for the possibility that amounts of a given process stream may be removed where appropriate for reducing equipment loading, prevention of byproduct accumulation, sampling, etc.

Whereas processes for producing para-xylene utilize the above-mentioned steps and/or other steps as described herein, for example in forming a para-xylene process flow loop, these processes do not preclude the possibility of one or more additional steps, or operations, occurring upstream and/or downstream of a recited step, such as mixing (e.g., with an auxiliary feed stream to a given step), separation (e.g., of an intermediate product stream), bypassing of a recited step (e.g., with a portion of a process stream), recycle back to a step (e.g., of a portion of a process stream), and/or reaction (e.g., to react undesired components and/or increase the yield of desired components). In the case of separation, representative additional steps or operations include the removal of dealkylated products (e.g., benzene), occurring downstream of the para-xylene separation zone or the removal of a fraction enriched in $C_7^-$ hydrocarbons, occurring downstream of the isomerization zone. In the case of recycle, a representative additional step or operation is the recycle of a portion of the xylene-equilibrated isomerate, downstream of the isomerization zone, back to the xylene separation zone. In the case of reaction, a representative additional step or operation is the transalkylation, or disproportionation, reaction between $C_7$ aromatic hydrocarbons (e.g., toluene) and $C_9$ aromatic hydrocarbons (e.g., trimethylbenzene) to produce xylenes, occurring downstream of the isomerization zone.

In some cases, however, processes may be performed without any one of, or any combination of, such mixing, separation, bypassing, recycle, and reaction, occurring upstream of, and/or downstream of, any one recited step, or any two or more recited steps. According to particular embodiments, processes may be performed with an additional step of separating a fraction enriched in $C_7^-$ hydrocarbons from the xylene-equilibrated isomerate and/or reacting at least a portion of the xylene-equilibrated isomerate in a transalkylation zone. In these embodiments, at least a portion of the resulting $C_7^-$ hydrocarbon-depleted, xylene-equilibrated isomerate and/or at least a portion of the resulting transalkylation zone effluent (having an increased concentration of xylenes, relative to the xylene-equilibrated isomerate), can be recycled to the xylene column, whereby these resulting streams nonetheless comprise at least a portion of the xylene-equilibrated isomerate.

Distillation steps described herein to provide fractions designated "overhead fraction" and "bottoms fraction" may be removed from the overhead or bottoms of a respective distillation column. However, an "overhead fraction" may otherwise be referred to as a "low-boiling fraction," which is meant to more broadly encompass any fraction having a higher volatility (lower boiling point range) and/or a lower distillation end point temperature, relative to a feed to, and/or relative to a "bottoms fraction" from, the respective distillation column. Likewise, a "bottoms fraction" may otherwise be referred to as a "high-boiling fraction," which is meant to more broadly encompass any fraction having a lower volatility (higher boiling point range) and/or a higher initial boiling point temperature, relative to a feed to, and/or relative to an overhead fraction from, the respective distillation column, with the overhead fraction being as defined above. Initial boiling point and end point temperatures may be determined according to ASTM D86.

The process parameters of ethylbenzene conversion and aromatic ring loss, on the basis of "once through" the isomerization zone (e.g., isomerization reactor in this zone) and on the basis of overall conversion (i.e., conversion of ethylbenzene introduced into the para-xylene process flow loop and loss of aromatic rings introduced into the para-xylene process flow loop, are as defined herein. The yield of para-xylene may likewise be determined on a "per-pass" (once-through) or "overall" basis. The per-pass yield, or recovery, refers to the total para-xylene input to the xylene separation zone (e.g., the para-xylene in the $C_8$ aromatic hydrocarbon stream, or portion thereof, or otherwise the combined para-xylene in the ethylbenzene-depleted, $C_8$ aromatic hydrocarbon stream and portion of the $C_8$ aromatic hydrocarbon stream bypassing the extractive distillation) that is present in the para-xylene rich product, output from the xylene separation zone. The overall yield refers to the total xylenes input to the process, such as input to para-xylene process flow loop as described herein (e.g., total xylenes in the impure ethylbenzene-containing feed) that are present as para-xylene in the para-xylene rich product. Therefore, the per-pass yield is based on 100% yield being the total recovery of para-xylene, input to the xylene separation zone, in the para-xylene rich product, whereas the overall yield is based on 100% yield being the total conversion of ortho-xylene and meta-xylene, input to the process, to para-xylene (i.e., the recycle of these isomers to extinction in the para-xylene process flow loop) and therefore total recovery of all xylenes input to the process as para-xylene.

In a para-xylene separation zone comprising either adsorptive separation or crystallization, the per-pass yield and/or the overall yield of para-xylene may be greater than about 60%, greater than about 90%, greater than about 95%, or greater than about 98%. The purity of the para-xylene rich product is generally such that it comprises greater than about 93% by weight (wt-%), greater than about 97 wt-%, greater than about 99 wt-%, or even greater than about 99.7 wt-% of para-xylene. Those skilled in the art will appreciate that there is generally a tradeoff between para-xylene recovery, or per-pass yield, and para-xylene purity, according to a "purity/recovery curve" that is associated with a given process.

The impure ethylbenzene-containing feed to processes described herein comprises any mixture of ethylbenzene and xylenes, from which para-xylene may be recovered in an economically favorable manner, using a combination of para-xylene separation and isomerization of the resulting para-xylene-depleted effluent (e.g., raffinate or reject filtrate). Representative impure ethylbenzene-containing feeds comprise $C_8$ aromatic hydrocarbons in a combined amount of greater than about 50 wt-%, greater than about 75 wt-%, or greater than about 95 wt-%. At least a portion of the balance of such feeds may be $C_9^+$ hydrocarbons, including $C_9$ aromatic hydrocarbons. For example, impure ethylbenzene-containing feeds may comprise $C_9^+$ hydrocarbons in an amount of less than about 20 wt-%, less than about 10 wt-%, or less than about 5 wt-%. Generally, all or substantially all (e.g., greater than about 95 wt-%) of such $C_9^+$ hydrocarbons may be conveniently removed in a xylene column as described herein, and/or in an EB separation unit. In carrying out such removal, the resulting $C_8$ aromatic hydrocarbon stream that may be obtained, for example as an overhead fraction or low-boiling fraction from the xylene column, may comprise $C_8$ aromatic hydrocarbons in a combined amount of greater than about 85 wt-%, greater than about 95 wt-%, or greater than about 98 wt-%.

In the case of either the impure ethylbenzene-containing feed or the $C_8$ aromatic hydrocarbon stream (e.g., $C_8$ aromatic hydrocarbon fraction of this feed), ethylbenzene may be present in an amount generally from about 3 wt-% to about 75 wt-%, depending on the source of the impure ethylbenzene-containing feed. For example, the impure ethylbenzene-containing feed may comprise a product of naphtha reforming (e.g., a reformate), a product of naphtha cracking (e.g., pyrolysis gasoline), a product of transalkylation (e.g., an effluent from the reaction of toluene and $C_9$ aromatic hydrocarbons to produce $C_8$ aromatic hydrocarbons), or any combination of one or more of such products. In the case of an impure ethylbenzene-containing feed comprising, consisting of, or consisting essentially of (e.g., comprising greater than 95 wt-% of) a product of naphtha reforming, ethylbenzene may be present in the feed in an amount from about 5 wt-% to about 45 wt-% or from about 10 wt-% to about 35 wt-%. In the case of an impure ethylbenzene-containing feed comprising, consisting of, or consisting essentially of (e.g., comprising greater than 95 wt-% of) a product of naphtha cracking (e.g., pyrolysis gasoline), ethylbenzene may be present in the feed in an amount from about 25 wt-% to about 75 wt-% or from about 35 wt-% to about 65 wt-%. In the case of an impure ethylbenzene-containing feed comprising, consisting of, or consisting essentially of (e.g., comprising greater than 95 wt-% of) a product of transalkylation, ethylbenzene may be present in the feed in amount from about 1 wt-% to about 25 wt-% or from about 2 wt-% to about 15 wt-%. Representative products of naphtha reforming naphtha cracking, and/or transalkylation include those products from which benzene and toluene have been separated upstream in an overhead fraction, for example using a reformate splitter as described herein.

EMBODIMENTS OF THE INVENTION

Embodiments of the invention are directed to a process for producing para-xylene, the process comprising: in a xylene column, separating a $C_8$ aromatic hydrocarbon stream and a $C_9^+$ hydrocarbon stream, from an impure ethylbenzene-containing feed. The $C_8$ aromatic hydrocarbon stream may represent a low-boiling fraction, being enriched in $C_8$ aromatic hydrocarbons and depleted in $C_9^+$ hydrocarbons, relative to the impure ethylbenzene-containing feed, whereas the $C_9^+$ hydrocarbon stream may represent a high boiling fraction, being enriched in $C_9^+$ hydrocarbons and depleted in $C_8$ aromatic hydrocarbons, relative to the impure ethylbenzene stream. Representative impure ethylbenzene-containing feeds comprise a mixture of ethylbenzene and xylenes, such as a mixture obtained from products of naphtha reforming (e.g., a reformate), naphtha cracking (e.g., a pyrolysis gasoline), and/or transalkylation (e.g., products of conversion of toluene and $C_9$ aromatic hydrocarbons to $C_8$ aromatic hydrocarbons). For example, such mixtures may be obtained following the removal of $C_7^-$ hydrocarbons from such products, in a low-boiling fraction that is separated in an upstream splitter.

The process may further comprise: in a xylene separation zone, separating a para-xylene rich product from at least a portion of the $C_8$ aromatic hydrocarbon stream, to provide a para-xylene-depleted effluent. In the case of a xylene separation zone utilizing a simulated moving bed (SMB) adsorption process, the para-xylene-depleted effluent may be a raffinate obtained from this process, as described above. In the case of a xylene separation zone utilizing crystallization, the para-xylene-depleted effluent may be a reject filtrate, as described above.

The process may further comprise: in an isomerization zone, isomerizing at least a portion of the para-xylene-depleted effluent, to provide a xylene-equilibrated isomerate. This product may have concentrations of the xylene isomers (ortho-xylene, meta-xylene, and para-xylene) approaching their equilibrium concentrations to a greater extent, relative to the para-xylene-depleted effluent. The xylene-equilibrated isomerate may also be enriched in (or have a higher concentration of) para-xylene, relative to the para-xylene-depleted effluent. The process may additionally comprise recycling at least a portion, and preferably all, of the xylene-equilibrated isomerate to the xylene column. This recycling may result in a para-xylene process flow loop, as described in greater detail herein.

The isomerization zone, or an isomerization reactor within this zone, may operate as described herein, with relatively low levels of ethylbenzene conversion and/or aromatic ring loss, either of which parameters may be measured on a "per-pass" (once-through) basis, from the isomerization zone (or isomerization reactor) inlet (e.g., the para-xylene-depleted effluent) to the isomerization zone (or isomerization reactor) outlet (e.g., the xylene-equilibrated isomerate).

For example, the per-pass ethylbenzene conversion may be determined, on a percentage basis, according to:

$$[1-(EB_{RXOUT}/EB_{RXIN})] \times 100,$$

in which $EB_{RXOUT}$ represents the weight of ethylbenzene output from an isomerization reactor (e.g., present in the xylene-equilibrated isomerate) and $EB_{RXIN}$ represents the weight of ethylbenzene input to the isomerization reactor (e.g., present in the para-xylene-depleted effluent or portion thereof being fed to this reactor). These weights of ethylbenzene input to, or output from, an isomerization reactor, may be calculated (e.g., during steady-state operation) from the percentage by weight of ethylbenzene in the relevant input and output process stream(s), multiplied by the respective weights, or mass flow rates, of these stream(s). In representative embodiments, operation of the isomerization zone (or isomerization reactor in this zone) is carried out with a per-pass ethylbenzene conversion of less than about 5%, less than about 2%, or even less than about 1%.

The per-pass aromatic ring loss may be determined, on a percentage basis, according to:

$$NONAROM_{RXDELTA}/AROM_{RXIN} \times 100,$$

in which $NONAROM_{RXDELTA}$ represents the number of moles of non-aromatic hydrocarbons generated in an isomerization reactor (e.g., moles present in the xylene-equilibrated isomerate minus moles present in the para-xylene effluent or portion thereof being fed to this reactor) and $AROM_{RXIN}$ represents the number of moles of aromatic hydrocarbons input to the isomerization reactor (e.g., moles present in the para-xylene effluent or portion thereof being fed to this reactor). These numbers of moles of non-aromatic hydrocarbons generated in an isomerization reactor, as well as numbers of moles of aromatic hydrocarbons input to this reactor, may be calculated (e.g., during steady-state operation) from the percentages by weight of non-aromatic and aromatic hydrocarbons, divided by their respective molecular weights, in the relevant input and output stream(s), and multiplied by the weights, or mass flow rates, of the respective stream(s). In representative embodiments, operation of the isomerization zone (or isomerization reactor in this zone) is carried out with a per-pass aromatic ring loss of less than about 5%, less than about 2%, or even less than about 1%.

The parameters of ethylbenzene conversion and aromatic ring loss may otherwise be measured on an "overall" basis, from the total inputs to the process (e.g., the impure ethylbenzene-containing feed) to the total outputs from the process (e.g., the para-xylene rich product, the ethylbenzene-rich product, the non-aromatic compound-enriched stream, and the $C_9^+$ hydrocarbon stream). The total inputs and outputs may therefore be those inputs and outputs to a para-xylene process flow loop, as described herein, or may otherwise include additional inputs and outputs added to, or removed from, this loop (e.g., an output that is a $C_7^-$ rich effluent removed as an overhead fraction from a deheptanizer column). The overall ethylbenzene conversion and overall aromatic ring loss may therefore be determined, respectively, according to $$1-(EB_{PROCESSOUT}/EB_{PROCESSIN}) \times 100 \text{ and } NON\text{-}AROM_{PROCESSDELTA}/AROM_{PROCESSIN} \times 100,$$

in a manner analogous to that described above with respect to these parameters being determined on a per-pass basis. Therefore, $EB_{PROCESSOUT}$ and $EB_{PROCESSIN}$ represent, respectively, the weight of ethylbenzene output from, and input to, the process (e.g., output from and input to a para-xylene process flow loop, as described herein), and $NONAROM_{PROCESSDELTA}$ and $AROM_{PROCESSIN}$ represent, respectively, the number of moles of non-aromatic hydrocarbons generated in the process and the number of moles of aromatic hydrocarbons input to the process. In representative embodiments, operation of the process is carried out with an overall ethylbenzene conversion of less than about 50%, less than about 20%, less than about 10%, or even less than about 2%. These ranges can therefore represent the percentage conversion of ethylbenzene, introduced into the para-xylene process flow loop (e.g., under steady-state conditions). In further representative embodiments, operation of the process is carried out with an overall aromatic ring loss of less than about 10%, less than about 5%, or even less than about 2%. These ranges can therefore represent the percentage loss of aromatic rings, introduced into the para-xylene process flow loop (e.g., under steady-state conditions).

Whether determined on a per-pass or overall basis, the relatively low levels of ethylbenzene conversion and aromatic ring loss, compared to conventional processes, may reside in reduced requirements of the isomerization zone in terms of ethylbenzene conversion (e.g., by isomerization or cracking as described above) and correspondingly milder operating conditions and/or simplified isomerization catalyst formulations. These effects, in combination, can promote increased para-xylene yields; reduced utility requirements, hydrogen consumption, and byproduct yields; and the generation of a high value ethylbenzene-rich product.

According to representative embodiments, extractive distillation or other separation method (e.g., occurring in an EB separation unit) is used to remove ethylbenzene from at least a portion of one or more streams identified above (e.g., the impure ethylbenzene-containing feed, the $C_8$ aromatic hydrocarbon stream, the para-xylene-depleted effluent, and/or the xylene-equilibrated isomerate). According to further representative embodiments, following this ethylbenzene separation (e.g., to generate an ethylbenzene-rich product), at least a portion of the resulting ethylbenzene-depleted stream (e.g., the ethylbenzene-depleted $C_8$ aromatic hydrocarbon stream, the ethylbenzene-, para-xylene-depleted effluent, and/or the ethylbenzene-depleted, xylene-equilibrated isomerate) is combined with a portion of the stream bypassing the extractive distillation. That is, at least a portion of the one or more streams identified above is used as a feed to an EB separation unit (e.g., an extractive distillation zone), and the resulting ethylbenzene-depleted stream is returned to the process (e.g., returned to the para-xylene process flow loop) in the same stream (e.g., without having the stream bypassing the EB separation unit being subjected to any intervening separation or conversion, prior to being combined with the resulting ethylbenzene-depleted stream).

Accordingly, the portion of a given process stream bypassing the EB separation unit may refer to that which is diverted from the portion used as the feed to this unit, and which bypassing portion forms all or part of a stream of the para-xylene process flow loop, such as all or part of (i) the $C_8$ aromatic hydrocarbon stream, (ii) the para-xylene depleted effluent, or (iii) the xylene-equilibrated isomerate, as described herein. Preferably, the bypassing portion forms the stream the of para-xylene process flow loop, corresponding to the portion used as the feed to the EB separation unit, for example in the case of (i) a portion of the $C_8$ aromatic hydrocarbon stream being fed to the EB separation unit, and the bypassing portion forming the $C_8$ aromatic hydrocarbon stream of the para-xylene process flow loop; (ii) a portion of the para-xylene depleted effluent being fed to the EB separation unit, and the bypassing portion forming the para-xylene depleted effluent of the para-xylene process flow loop, or (iii) a portion of the xylene-equilibrated isomerate being fed to the EB separation unit, and the bypassing portion forming the xylene-equilibrated isomerate of the para-xylene process flow loop. It is also possible, in the case of separating an ethylbenzene-rich product from all or a portion of the impure ethylbenzene containing feed, to combine the resulting ethylbenzene-depleted feed with all or a portion of the $C_8$ aromatic hydrocarbon stream. In this case, a portion of the impure ethylbenzene-containing feed bypassing the EB separation unit (bypassing portion) may form all or a portion of the fresh feed to the xylene column, such that a fraction of this fresh feed, namely that contained in the $C_8$ aromatic hydrocarbon stream removed as an overhead fraction from the xylene column, may be introduced to the para-xylene process flow loop. In this regard, particular aspects of the invention are associated with improvements in processing flexibility in the operation of para-xylene production processes. Advantageously, smaller or greater quantities of feed portions of a given process stream may be fed to an EB separation unit, regardless of where it is positioned along the para-xylene processing flow loop, and respectively greater or smaller quantities of bypassing portions of the stream may be used to form this loop. This provides important benefits in terms of adjusting the process to accommodate impure ethylbenzene-containing feeds of varying quality (e.g., ethylbenzene content), in view of the economic tradeoff between processing more throughput in the EB separation unit, with the potential to achieve greater ethylbenzene recovery, and otherwise processing more throughput in the para-xylene process flow loop, with the potential to reduce the process demands (e.g., utilities) of the EB separation unit.

Advantageously, representative processes may further comprise removal, without conversion, of all or substantially all (e.g., greater than about 80%, greater than about 90%, or greater than about 95%) of the ethylbenzene introduced into the process, such as the para-xylene process flow loop as described herein. The extent of ethylbenzene conversion, which may be measured on a per-pass or overall basis as described herein, will depend on the operating conditions and catalyst used in the isomerization reaction zone (e.g., isomerization reactor conditions and catalyst), which, as discussed above, may lead to reduced side reactions, relative to conventional processes that do not utilize extractive distillation for ethylbenzene separation. With respect to this process loop, all or substantially all (e.g., greater than about 80%, greater than about 90%, or greater than about 95%) of the ethylbenzene introduced may be present in the impure ethylbenzene-containing feed to the xylene column. The extent of ethylbenzene introduction into the process loop will depend on the operation of the xylene column and its efficiency in separating ethylbenzene into the $C_8$ aromatic hydrocarbon stream.

Para-Xylene Production Process and Process Flow Loop

According to the representative process depicted in FIG. 1, impure ethylbenzene-containing feed 2, as described above, is fed to xylene column 100 for separating $C_8$ aromatic hydrocarbon stream 4 as a low-boiling fraction (or overhead fraction) and $C_9^+$ hydrocarbon stream 12 as a high-boiling fraction (or bottoms fraction). A portion 4A of $C_8$ aromatic hydrocarbon stream 4 is fed to EB separation unit (e.g., extractive distillation zone) 400 for separating ethylbenzene-rich product 402, and optionally also non-aromatic compound enriched stream 401, and provide ethylbenzene-depleted $C_8$ aromatic hydrocarbon stream 4B. Non-aromatic compound-enriched stream 401, if produced, is enriched in (or has a higher concentration of) non-aromatic compounds, relative to $C_8$ aromatic hydrocarbon stream 4. Non-aromatic hydrocarbons present in non-aromatic compound-enriched stream 401 may include $C_8$ paraffinic hydrocarbons (e.g., n-octane and isomers of iso-octane), $C_7$-$C_8$ cycloparaffinic hydrocarbons (e.g., ethylcyclohexane and cyclooctane), and/or $C_9$ naphthenic hydrocarbons (e.g., isomers of trimethylcyclohexane), having boiling points close to those of $C_8$ aromatic hydrocarbons. Non-aromatic compound-enriched stream 401 may comprise greater than about 75 wt-%, greater than about 85 wt-%, or greater than about 95 wt-% of non-aromatic hydrocarbons.

Ethylbenzene-rich product 402 may comprise predominantly ethylbenzene, and preferably comprises ethylbenzene at a high concentration, suitable for direct use in styrene monomer production. For example, ethylbenzene-rich product 402 may comprise ethylbenzene in an amount of greater than about 90 wt-%, greater than about 95 wt-%, greater than about 98 wt-%, greater than about 99 wt-%, or greater than about 99.5 wt-%. Ethylbenzene-rich product 402 from EB separation unit 400, for example obtained from extractive distillation, therefore represents a high value product that may be recovered from a para-xylene production processes as described herein. Accordingly, such a process may alternatively be referred to as a para-xylene and ethylbenzene production process. Ethylbenzene-depleted $C_8$ aromatic hydrocarbon stream 4B is depleted in (or has a lower concentration of) ethylbenzene, relative to $C_8$ aromatic hydrocarbon stream 4. According to the embodiment depicted in FIG. 1, ethylbenzene-depleted $C_8$ aromatic hydrocarbon stream 4B from EB separation unit 400 is combined with portion 40 of $C_8$ aromatic hydrocarbon stream 4 bypassing this unit, to provide combined feed 45 to xylene separation zone 200.

In para-xylene separation zone 200, para-xylene rich product 10, as described above, is separated, for example using adsorptive separation or crystallization, to provide para-xylene-depleted effluent 6 (e.g., as a para-xylene-depleted raffinate of an SMB adsorptive separation process or as a para-xylene-depleted reject filtrate of a crystallization process). In general, para-xylene-depleted effluent 6 is depleted in (or has a lower concentration of) para-xylene, relative to combined feed 45, or otherwise relative to $C_8$ aromatic hydrocarbon stream 4. For example, para-xylene-depleted effluent 6 may comprise para-xylene in an amount of less than about 10 wt-%, less than about 5 wt-%, or less than about 2 wt-%.

Para-xylene-depleted effluent 6 is fed to isomerization zone 300 for isomerizing this effluent, to provide xylene-equilibrated isomerate 8, having concentrations of the xylene isomers (ortho-xylene, meta-xylene, and para-xylene) approaching their equilibrium concentrations to a greater extent, relative to para-xylene-depleted effluent 6. In general, xylene-equilibrated isomerate 8 is also enriched in (or has a higher concentration of) para-xylene, relative to para-xylene-depleted effluent 6. For example, xylene-equilibrated isomerate 8 may comprise para-xylene in an amount of greater than about 10 wt-%, greater than about 20 wt-%, or greater than about 30 wt-%. All or a portion of xylene-equilibrated isomerate 8 may then be recycled to xylene column 100.

Figure 2:
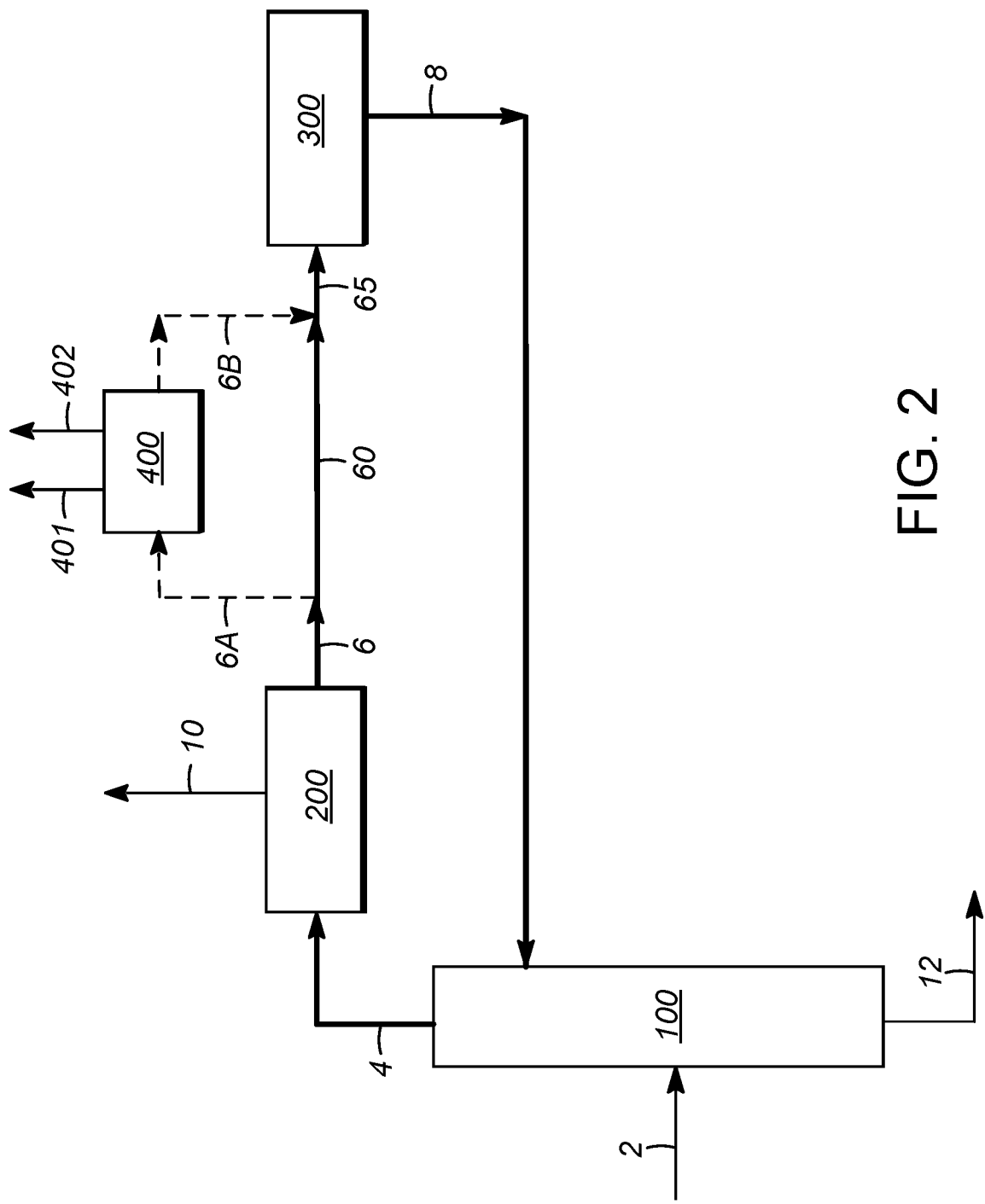
Figure 3:
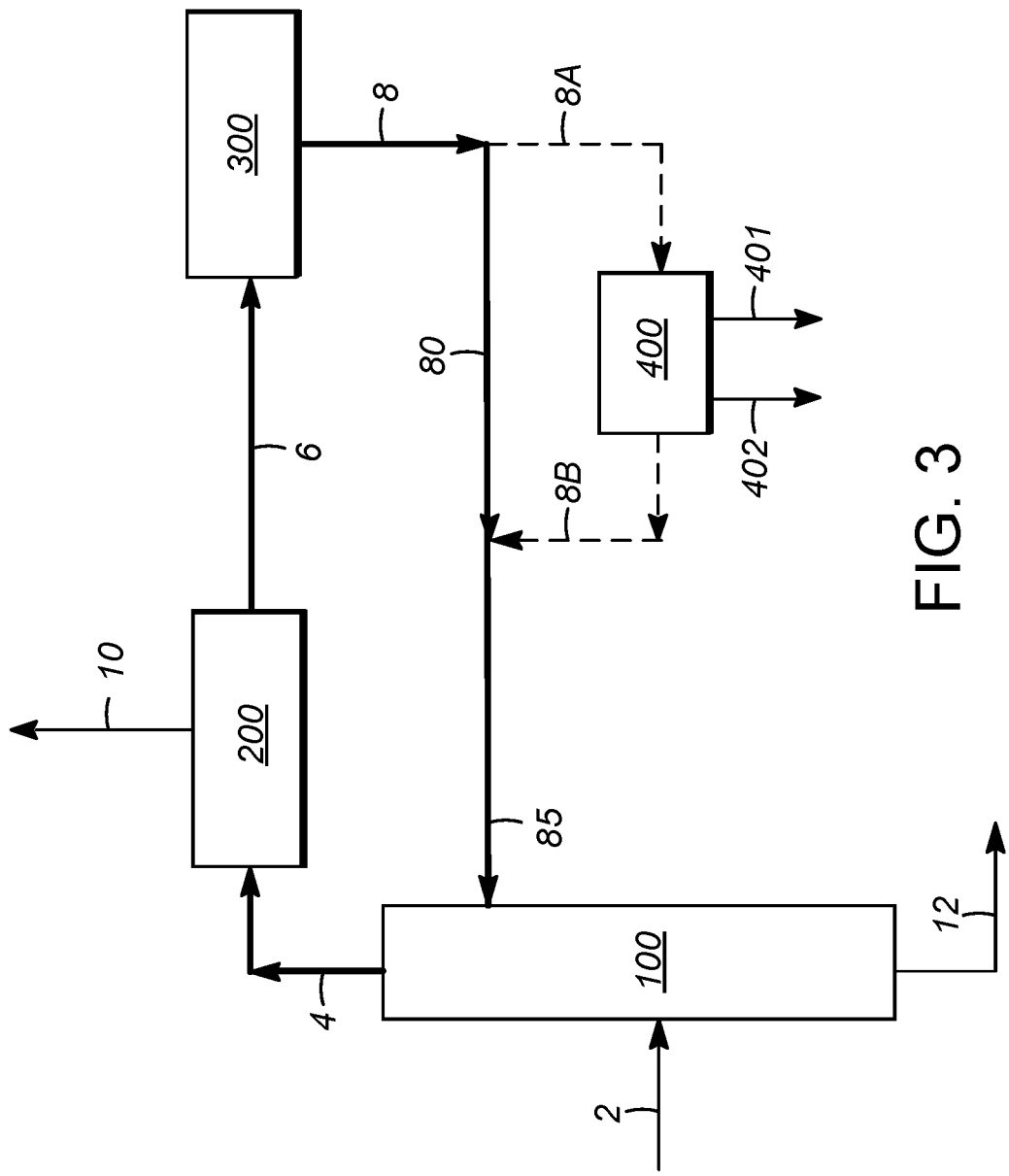

According to the alternative embodiments depicted in FIGS. 2 and 3, it can be appreciated that EB separation unit 400 may be utilized to remove ethylbenzene from different streams of the process. Whereas these figures illustrate returning, or re-combining, the respective ethylbenzene-depleted streams back to the same stream from which a portion thereof was subjected to EB separation (e.g., by extractive distillation), in general such ethylbenzene-depleted streams can be returned elsewhere to the process or otherwise used for alternative purposes. As shown in FIG. 2, a portion 6A of para-xylene-depleted effluent 6 is fed to EB separation unit 400 for separating, for example by extractive distillation, both non-aromatic compound-enriched stream 401 and ethylbenzene-rich product 402, as described above. EB separation unit 400 provides ethylbenzene, para-xylene-depleted effluent 6B, which is depleted in (or has a lower concentration of) ethylbenzene, relative to para-xylene-depleted effluent 6. As further shown in FIG. 2, ethylbenzene, para-xylene-depleted effluent 6B from EB separation unit 400 is combined with portion 60 of para-xylene-depleted effluent 6 bypassing this unit, to provide combined feed 65 to isomerization zone 300.

As shown in FIG. 3, a portion 8A of xylene-equilibrated isomerate 8 is fed to EB separation unit 400 for separating, for example by extractive distillation, both non-aromatic compound-enriched stream 401 and ethylbenzene-rich product 402, as described above. EB separation unit 400 provides ethylbenzene-depleted, xylene-equilibrated isomerate 8B, which is depleted in (or has a lower concentration of) ethylbenzene, relative to xylene-equilibrated isomerate 8. As further shown in FIG. 3, ethylbenzene-depleted, xylene-equilibrated isomerate 8B from EB separation unit 400 is combined with portion 80 of xylene-equilibrated isomerate 8 bypassing this unit, to provide combined recycle 85 to xylene column 100.

In some cases, the embodiment depicted in FIG. 3, in which ethylbenzene-rich product 402 is separated from portion 8A of xylene-equilibrated isomerate 8, may provide additional advantages. These may be associated with providing residual amounts of extractive agent, used in EB separation unit (e.g., extractive distillation zone) 400, directly to xylene column 100, and not to para-xylene separation zone 200 or isomerization zone 300, where such extractive agent might interfere with the operations occurring in these zones. Minor losses of extractive agent from extractive distillation zone 400 may, for example, lead to its presence in ethylbenzene-depleted streams 4B, 6B, 8B, as described above, and an expedient solution may therefore be its immediate removal in $C_9^+$ hydrocarbon stream, separated in xylene column 100.

According to each of the embodiments depicted in FIGS. 1-3, it can be appreciated that such processes comprise forming a para-xylene process flow loop comprising: (i) $C_8$ aromatic hydrocarbon stream 4 (or portion 40 thereof), separated as a low-boiling fraction (or overhead fraction) in xylene column 100, (ii) para-xylene-depleted effluent 6 (or portion 60 thereof), separated in xylene separation zone 200 from $C_8$ aromatic hydrocarbon stream 4 (or portion 40 thereof), and (iii) xylene-equilibrated isomerate 8 (or portion 80 thereof), provided from isomerization of para-xylene-depleted effluent 6 (or portion 60 thereof) in isomerization zone 300. The process may be completed by recycling xylene-equilibrated isomerate 8 (or portion 80 thereof) to xylene column 100. Advantageously, EB separation unit 400 may be used to remove ethylbenzene-rich product 402 from this loop, in order to obtain the simultaneous advantages of reducing ethylbenzene concentration in the loop and recovering it as a high value product. According to representative embodiments, each of $C_8$ aromatic hydrocarbon stream 4, para-xylene-depleted effluent 6, and xylene-equilibrated isomerate 8, comprises less than about 25 wt-% of ethylbenzene. As more particularly illustrated in FIGS. 1-3, impure ethylbenzene-containing feed 2 may be continuously input to this loop, whereas ethylbenzene-rich product 402, para-xylene rich product 10, and optionally non-aromatic enriched stream 401, may be continuously output from this loop, with the accumulation of ethylbenzene and optionally non-aromatic compounds in this loop being controlled by the integration with EB separation unit 400. Particular types of non-aromatic compounds that may be present in non-aromatic enriched stream 401, and that may therefore be separated from the para-xylene process flow loop, include non-aromatic hydrocarbons, such as those described above, namely $C_8$ paraffinic hydrocarbons (e.g., n-octane and isomers of iso-octane), $C_7$-$C_8$ cycloparaffinic hydrocarbons (e.g., ethylcyclohexane and cyclooctane), and/or $C_9$ naphthenic hydrocarbons (e.g., isomers of trimethylcyclohexane).

Figure 4:
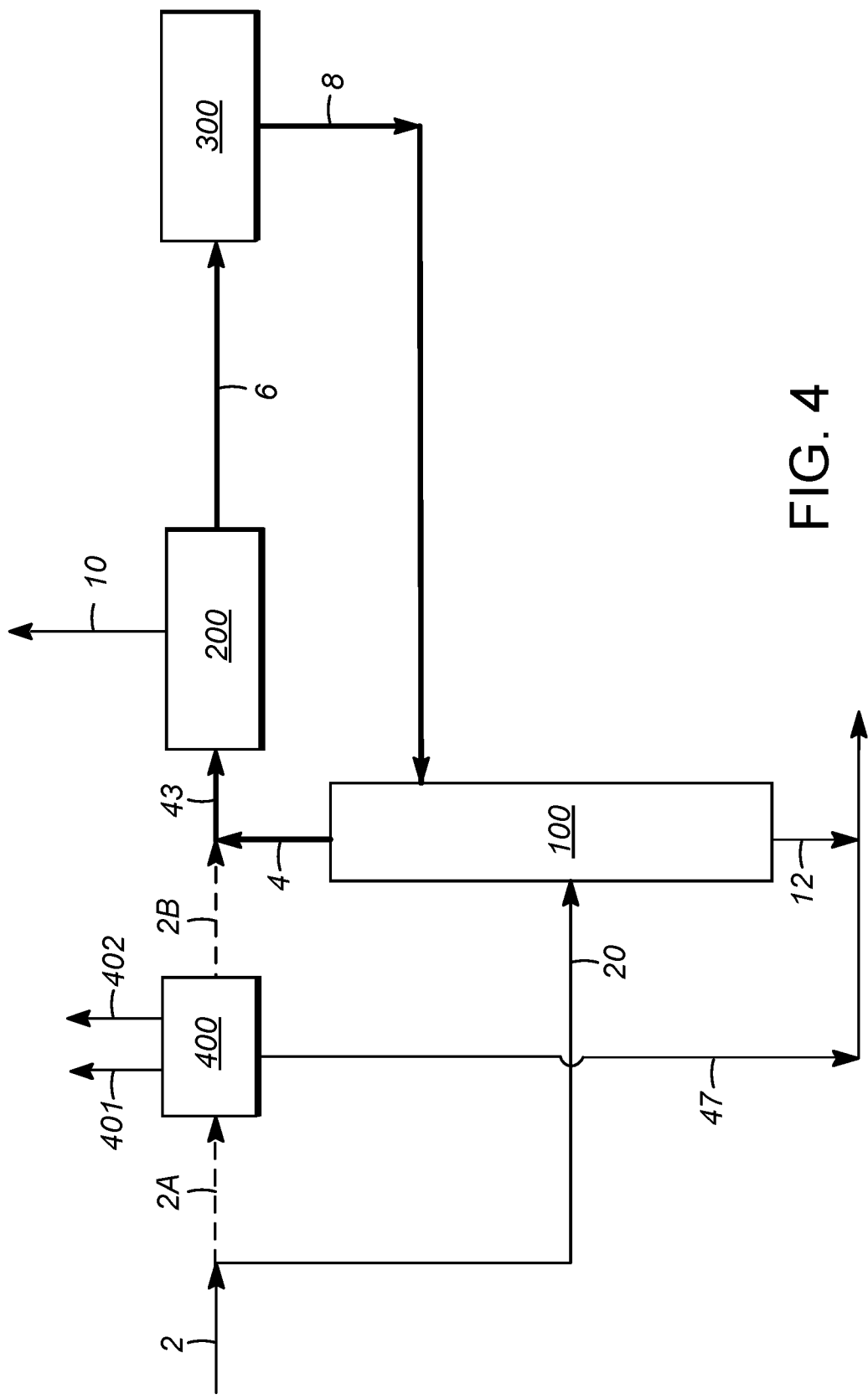

FIG. 4 illustrates yet another embodiment, in which ethylbenzene and optionally non-aromatic compounds are likewise separated from the process. However, in this embodiment, ethylbenzene-rich product 402, and optionally non-aromatic enriched stream 401, are separated using EB separation unit 400, being fed with all or a portion of impure ethylbenzene-containing feed 2. That is, the process according to this embodiment may comprise separating ethylbenzene-rich product 402 from all of impure ethylbenzene-containing feed 2, or otherwise portion 2A of this feed, in which case portion 20 bypassing EB separation unit is fed to xylene column 100. In either case, at least a portion of ethylbenzene-depleted feed 2B may be combined with C$_8$ aromatic hydrocarbon stream 4, separated as a low-boiling fraction (e.g. overhead fraction) from xylene column 100, to provide combined, ethylbenzene-depleted feed/C$_8$ aromatic hydrocarbon stream 43. At least a portion of this stream 43 may then be fed to xylene separation zone 200, such that this stream 43, in combination with C$_8$ aromatic hydrocarbon stream 4, para-xylene-depleted effluent 6, and xylene-equilibrated isomerate 8, may form a para-xylene process flow loop as described above with respect to the embodiments depicted in FIGS. 1-3. The embodiment depicted in FIG. 4, however, differs in that ethylbenzene is separated upstream of (prior to) this loop. Therefore, whereas parameters such as the overall yield of para-xylene, the overall conversion of ethylbenzene, and the overall aromatic ring loss may be within the ranges as described above, these parameters may be determined on the basis of the total xylenes, ethylbenzene, and aromatic hydrocarbons input to the process in impure ethylbenzene-containing feed (e.g., in portion 2A to EB separation unit 400 and portion 20 bypassing this unit), upstream of the para-xylene process flow loop. In addition, other parameters associated with this loop, such as the concentration of ethylbenzene, may be as described above, for example with respect to the embodiments depicted in FIGS. 1-3.

According to the embodiment depicted in FIG. 4, EB separation unit 400, for example comprising extractive distillation, may further provide, in addition to ethylbenzene-rich product 402, C$_9^+$ hydrocarbon-enriched heavy fraction 47. This fraction 47 may be combined with C$_9^+$ hydrocarbon stream 12, separated from xylene column 100.

In controlling the extent of accumulation of ethylbenzene in the para-xylene process flow loop, the portions 4A, 6A, 8A of respective C$_8$ aromatic hydrocarbon stream 4, para-xylene-depleted effluent 6, and/or xylene-equilibrated isomerate 8 that are diverted from this loop for ethylbenzene separation, or otherwise portion 2A of impure ethylbenzene-containing feed (embodiment of FIG. 4), can be varied. By increasing portions 2A, 4A, 6A, 8A, the concentration of ethylbenzene in the loop is directionally decreased, and process requirements (e.g., equipment and utilities) associated with streams making up the loop, such as para-xylene separation zone 200 and isomerization zone 300, are also decreased. However, processing requirements of EB separation unit 400 are increased. Conversely, by decreasing portions 2A, 4A, 6A, 8A, the concentration of ethylbenzene in the loop is directionally increased, and process requirements (e.g., equipment and utilities) associated with streams making up the loop, such as para-xylene separation zone 200 and isomerization zone 300, are also increased. However, processing requirements of EB separation unit 400 are decreased. Those having skill in the art, with knowledge of the present specification, will appreciate that a given, integrated para-xylene production/extractive distillation process can be operated with consideration of these tradeoffs.

For purposes of characterizing the tradeoffs between portion 4A, 6A, 8A withdrawn from the para-xylene process flow loop, or otherwise portion 2A of impure ethylbenzene-containing feed (embodiment of FIG. 4), and ethylbenzene concentration in this loop, the para-xylene-depleted effluent 6 and xylene-equilibrated isomerate 8 can serve as convenient references. These streams are both downstream of the para-xylene separation zone 200 and in general can have the same or approximately the same mass flow rate. According to representative embodiments, (i) the impure ethylbenzene-containing feed 2 or portion 2A thereof, (ii) the portion 4A of C$_8$ aromatic hydrocarbon stream 4, (iii) the portion 6A of the para-xylene-depleted effluent 6, or (iv) the portion 8A of the xylene-equilibrated isomerate 8, that is fed to EB separation unit 400 (or from which ethylbenzene-rich product 402 is separated) can represent generally from about 1 wt-% to about 95 wt-% of para-xylene-depleted effluent 6 or xylene-equilibrated isomerate 8. More typically, however, such portion 2A, 4A, 6A, 8A, or all of impure ethylbenzene-containing feed 2, represents from about 3 wt-% to about 50 wt-%, and often represents from about 5 wt-% to about 15 wt-%, of para-xylene-depleted effluent 6 or xylene-equilibrated isomerate 8, each normally having a comparable flow rate. According to further representative embodiments, (i) the impure ethylbenzene-containing feed 2 or portion 2A thereof, (ii) the portion 4A of C$_8$ aromatic hydrocarbon stream 4, (iii) the portion 6A of the para-xylene-depleted effluent 6, or (iv) the portion 8A of the xylene-equilibrated isomerate 8, that is fed to EB separation unit 400 (or from which ethylbenzene-rich product 402 is separated), can generally comprise from about 3 wt-% to about 50 wt-% of ethylbenzene. More typically, however, such portion 2A, 4A, 6A, 8A, or all of impure ethylbenzene-containing feed 2, comprises from about 10 wt-% to about 40 wt-%, and often comprises from about 15 wt-% to about 25 wt-%, of ethylbenzene.

According to more particular embodiments that are directed to desirable tradeoffs between portion 4A, 6A, 8A withdrawn from the para-xylene process flow loop, or otherwise portion 2A of impure ethylbenzene-containing feed (embodiment of FIG. 4), and ethylbenzene concentration in this loop, and preferably between (i) portion 2A, 4A, 6A, 8A, determined on the basis of the para-xylene-depleted effluent 6 or xylene-equilibrated isomerate 8 (e.g., the percentage flow rate of portion 2A, based on the flow rate of the para-xylene-depleted effluent 6 or xylene-equilibrated isomerate 8; the percentage flow rate of portion 4A, based on the flow rate of the para-xylene-depleted effluent 6 or xylene-equilibrated isomerate 8; the percentage flow rate of portion 6A, based on the flow rate of the para-xylene-depleted effluent 6; or the percentage flow rate of portion 8A, based on the flow rate of the xylene-equilibrated isomerate 8), and (ii) the concentration of ethylbenzene in the para-xylene-depleted effluent 6 or xylene-equilibrated isomerate 8, the value of (i) may be from about 5 wt-% to about 15 wt-% and the value of (ii) may be from about 15 wt-% to about 25 wt-%. For example, the value of (i) may be from about 7 wt-% to about 11 wt-% and the value of (ii) may be from about 16 wt-% to about 20 wt-%. Otherwise, with a lower portion withdrawn from the para-xylene process flow loop, or otherwise a lower portion 2A fed to EB separation unit 400 (embodiment of FIG. 4), and higher concentration of ethylbenzene in this loop, the value of (i) may be from about 4 wt-% to about 8 wt-% and the value of (ii) may be from about 23 wt-% to about 27 wt-%.

Isomerization Zone Conditions

In the operation of such para-xylene process flow loop, being integrated with an EB separation unit, such as an extractive distillation zone to prevent excess ethylbenzene accumulation in this loop, advantages reside in the reduced severity of operation of isomeration zone 300, such as associated with a reduced ethylbenzene conversion requirement, and corresponding reduced aromatic ring loss, as described above. Accordingly, in representative processes, a conversion of ethylbenzene introduced into the para-xylene process flow loop (e.g., during steady-state operation) is less than about 20%. In other representative processes, a loss of aromatic rings introduced into the para-xylene process flow loop (e.g., during steady-state operation) is less than about 5%.

The isomerization zone may comprise one or more individual isomerization reactors, containing a suitable isomerization catalyst in various catalyst bed configurations (e.g., fixed bed or moving bed) and flow configurations (e.g., axial flow or radial flow). Often, one reactor is used. In an isomerization reactor, typical isomerization conditions include a temperature from about 150° C. (302° F.) to about 500° C. (932° F.), and preferably from about 200° C. (392° F.) to about 300° C. (572° F.), as well as an absolute pressure from about 1.5 MPa (218 psi) to about 5 MPa (725 psi), and preferably from about 2.5 MPa (363 psi) to about 4.5 MPa (653 psi). Isomerization conditions may further include a weight hourly space velocity (WHSV), based on the weight flow of the para-xylene-depleted effluent and/or any other hydrocarbon-containing streams input to the isomerization reactor (e.g., ethylbenzene-, para-xylene-depleted effluent 6B as described above), from about 0.5 $hr^{-1}$ to about 20 $hr^{-1}$, and preferably from about 1 $hr^{-1}$ to about 10 $hr^{-1}$. As is understood in the art, the WHSV is the weight flow of the feed to a reactor, divided by the weight of the catalyst in the reactor and represents the equivalent catalyst bed weights of the feed stream processed every hour. The WHSV is related to the inverse of the reactor residence time.

Hydrogen may be introduced to an isomerization reactor, generally in a gaseous mixture (e.g., containing recycle hydrogen gas) at varying purity levels. A hydrogen-to-hydrocarbon molar ratio, based on the molar flow of the para-xylene-depleted effluent and/or any other hydrocarbon-containing streams input to the isomerization reactor (e.g., ethylbenzene-, para-xylene-depleted effluent 6B as described above) may be generally from about 0.5:1 to about 15:1, and typically from about 0.5:1 to about 10:1. Advantageously, however, in view of the reduced severity isomerization conditions that are possible with respect to processes as described herein, an isomerization reactor of isomerization zone 300 may be operated under liquid phase conditions and in the absence of added hydrogen. That is, the isomerization zone 300 may comprise an isomerization reactor, through which para-xylene-depleted effluent 6 or at least portion 60 thereof is passed in the liquid phase.

A reactor in isomerization reaction zone 300 generally comprises a catalyst, which may be functional for carrying out the desired isomerization of ortho-xylene and meta-xylene to para-xylene, but lack functionality for conversion of ethylbenzene, for example by isomerization or dealkylation (cracking). In this manner, catalyst formulations used in an isomerization reactor may advantageously be simplified, in view of the integration with extractive distillation zone 400 for ethylbenzene separation, relative to those formulated with the conventional requirement for ethylbenzene conversion. For example, the acidity of the isomerization catalyst support may be reduced and thereby promote a lower degree of ethylbenzene dealkylation and consequently a lower production of light hydrocarbons and other byproducts that cause a loss in yield of the desired para-xylene.

Representative isomerization catalysts used in an isomerization reaction zone comprise a metal component and a molecular sieve component that may be zeolitic or non-zeolitic, and optionally an inorganic oxide component. Representative zeolitic aluminosilicate molecular sieves include pentasil zeolites, such as those having the structure types of MFI, MEL, MTW, MFS, MTF and FER (IUPAC Commission on Zeolite Nomenclature), MWW, beta zeolite, or mordenite. Representative non-zeolitic molecular sieves include those having one or more of the AEL framework types, for example SAPO-11, or one or more of the ATO framework types, for example MAPSO-31 (see "Atlas of Zeolite Structure Types," Butterworth-Heineman, Boston, Mass., $3^{rd}$ ed., 1992). Representative metal components of isomerization catalysts include at least one noble metal and optionally at least one base metal modifier in addition to, or in place of, the at least one noble metal. Noble metals include platinum group metals selected from the group consisting of platinum, palladium, rhodium, ruthenium, osmium, iridium, and mixtures thereof. Base metals may be selected from the group consisting of rhenium, tin, germanium, lead, iron, cobalt, nickel, indium, gallium, zinc, uranium, dysprosium, thallium, and mixtures thereof. The metal component may also comprise combinations of one or more base metals and/or one or more noble metals. The total content of metal(s) in the isomerization catalyst is generally from about 0.01% to about 10% by weight, and typically from about 0.01% to about 3% by weight. The total content of the molecular sieve in the isomerization catalyst is generally from about 1% to about 99% by weight, typically from about 10% to about 90% by weight, and often from about 25% to about 75% by weight. Additional components of the isomerization catalyst may include an inorganic oxide component, such as binder material (e.g., alumina). A representative isomerization catalyst for use in an isomerization reactor comprises platinum in an amount as described above with respect to total metals content, on a zeolitic aluminosilicate molecular sieve.

Extractive Distillation Zone

As described herein, extractive distillation or other separation of ethylbenzene is performed in EB separation unit 400, on (i) the impure ethylbenzene-containing feed 2 or portion 2A thereof, (ii) the portion 4A of $C_8$ aromatic hydrocarbon stream 4, (iii) the portion 6A of the para-xylene-depleted effluent 6, or (iv) the portion 8A of the xylene-equilibrated isomerate 8, that is fed to this unit. For the sake of conciseness, this stream may generally be referred to as the portion 2A/4A/6A/8A fed to the EB separation unit (which portion 2A may represent all of impure ethylbenzene-containing feed 2), all or a fraction of which may be combined with one or more extractive agent compound(s) as described herein, to provide a liquid mixture. The extractive agent compound effectively contributes to the desired separation of ethylbenzene-rich product 402, by increasing the relative volatility of ethylbenzene to the other $C_8$ aromatic compounds (e.g., ortho-xylene, meta-xylene, and/or para-xylene). Moreover, the extractive agent compound is itself easily separated from a distillate (e.g., recovered as a bottoms fraction of the extractive distillation) that is enriched in the other $C_8$ aromatic compound(s) as well as the extractive agent compound, relative to portion 2A/4A/6A/8A fed to the EB separation unit, or otherwise a fraction of these respective streams. This allows for the convenient reuse (recycle) of the extractive agent compound, for example in a continuous extractive distillation process.

Representative extractive distillation processes comprise distilling a liquid mixture comprising portion 2A/4A/6A/8A fed to the EB separation unit (which portion 2A may represent all of impure ethylbenzene-containing feed 2), or otherwise a fraction thereof, and an extractive agent compound as described herein. The portion 2A/4A/6A/8A or fraction thereof may be considered a hydrocarbon component comprising ethylbenzene and one or more of the other $C_8$ aromatic compound(s). Accordingly, particular processes comprise distilling a liquid mixture comprising ethylbenzene, other $C_8$ aromatic compounds (e.g., ortho-xylene, meta-xylene, and/or para-xylene), and an extractive agent compound.

The performance of the extractive agent may be characterized according to its ability to increase relative volatility between ethylbenzene and at least one other $C_8$ aromatic compound to be separated (e.g., at least one of, at least two of, or all of, ortho-xylene, meta-xylene, and para-xylene), thereby increasing separation efficiency at each stage of vapor-liquid equilibrium. According to representative embodiments, the extractive agent compound(s) may be present in the liquid mixture in an amount such that the relative volatility (a) of ethylbenzene to at least one other $C_8$ aromatic compound is at least about 1.14, preferably at least about 1.16, more preferably at least about 1.20, and even more preferably at least about 1.22 at a given pressure, such as 200 millibar absolute pressure.

The performance of the extractive agent in extractive distillation processes described herein may alternatively be characterized by its competitive factor, with respect to ethylbenzene and the other $C_8$ aromatic compound(s) (e.g., ortho-xylene, meta-xylene, and/or para-xylene) to be separated from ethylbenzene. The competitive factor (D) can be quantified by the expression $$D = \frac{\frac{\text{weight ratio ethylbenzene}}{\text{other } C_8 \text{ aromatic compound}} \text{(with extractive agent compound)}}{\frac{\text{weight ratio ethylbenzene}}{\text{other } C_8 \text{ aromatic compound}} \text{(without extractive agent compound)}}.$$

The numerator of D is a vapor phase weight ratio of ethylbenzene to a given one of the other $C_8$ aromatic compound, at 80° C. (176° F.) and atmospheric pressure, in equilibrium with a liquid mixture of (i) 1 part by weight of 60 wt-% ethylbenzene and 40 wt-% of the other $C_8$ aromatic compound and (ii) 5 parts by weight of the extractive agent compound (or mixture of two or more extractive agent compounds). The denominator of D is a reference vapor phase weight ratio of the same compounds at 80° C. (176° F.) and atmospheric pressure, in equilibrium with the liquid composition of (i) only. Accordingly, values of D that exceed unity indicate an improvement in the ease of separability of ethylbenzene into the vapor phase, resulting from the presence of the extractive agent compound. This competitive factor may therefore be measured according to a standard protocol, for example as described herein. Advantageously, according to representative extractive distillation processes, the competitive factor may be generally at least about 1.10, typically at least about 1.18, and often at least about 1.20. Otherwise, an extractive agent may provide a competitive factor (D) that is less than unity, for example generally at most about 0.95, typically at most about 0.90, and often at most about 0.85, meaning that the extractive agent indicates an improvement in the ease of separability of the less volatile, further $C_8$ aromatic compound (e.g., meta-xylene or para-xylene) into the liquid phase.

Figure 5:
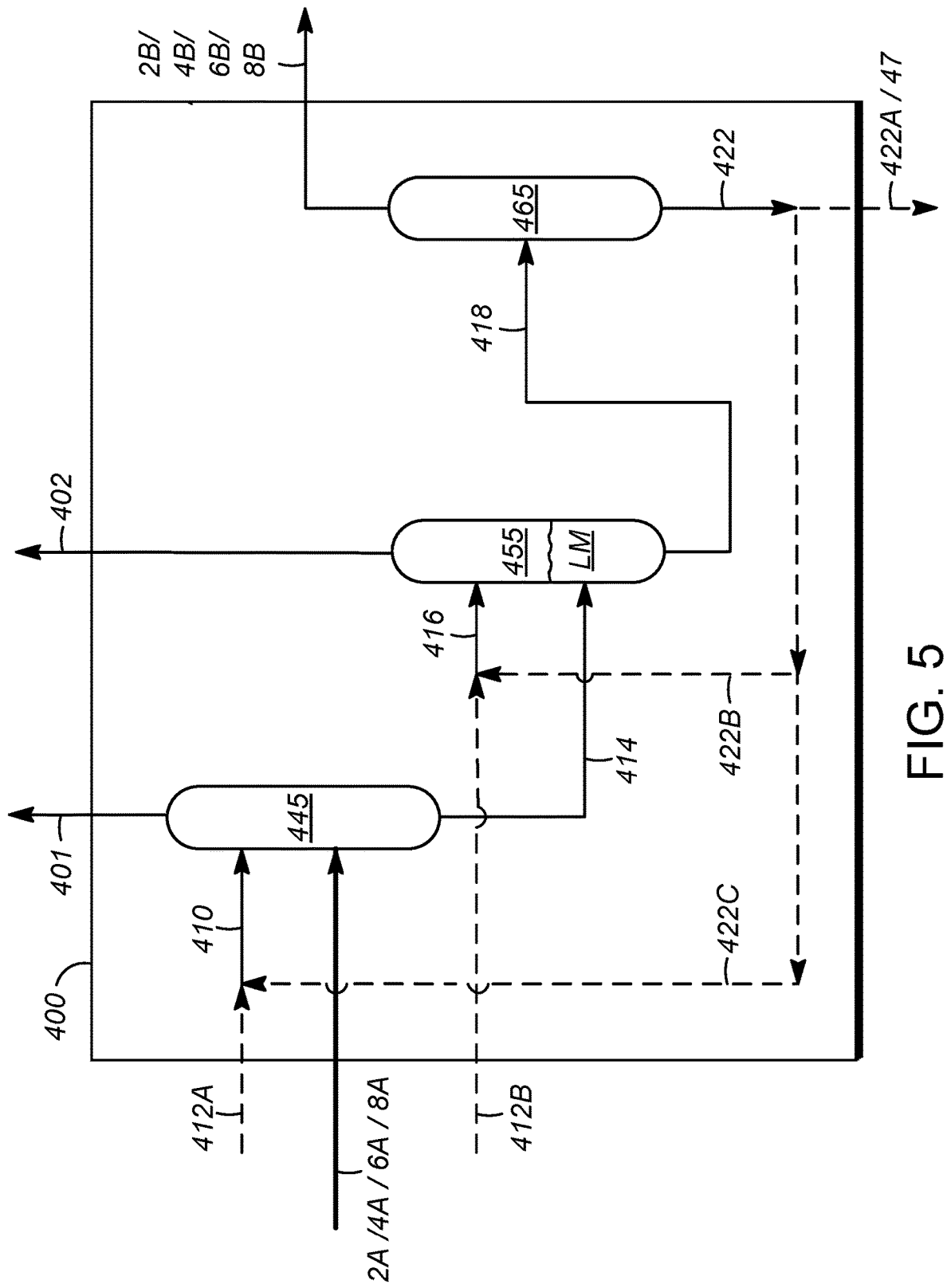
FIG. 5 depicts a representative extractive distillation process, for example that may serve as a particular type of EB separation unit that is integrated in a process depicted in FIGS. 1-4.

In some embodiments, alternative to, or in combination with, having a competitive factor, with respect to ethylbenzene and the other $C_8$ aromatic compound(s) as described above, a representative extractive agent compound or mixture of extractive agent compounds may have a competitive factor with respect to one or more non-aromatic hydrocarbons and ethylbenzene, which is greater than or less than unity. Advantageously, the extractive agent(s) can thereby facilitate the separation of such non-aromatic hydrocarbons from ethylbenzene and the other $C_8$ aromatic compound(s), for example by enriching such non-aromatic hydrocarbons in a low-boiling fraction or overhead removal fraction, as discussed in greater detail below in the case of non-aromatic removal column 445 (FIG. 5), upstream of extractive distillation column 455 (FIG. 5). According to some embodiments, representative extractive agent compound(s) may have a competitive factor D, determined in an analogous manner as described above but with the relevant weight ratios in the numerator and denominator being the weight ratio of a given non-aromatic compound to ethylbenzene, exceeding unity. According to particular embodiments, the extractive agent compound(s) may have a competitive factor D, (i) with respect to n-octane and ethylbenzene of generally at least about 2.0, typically at least about 2.3, and often at least about 2.6, (ii) with respect to ethylcyclohexane and ethylbenzene of generally at least about 1.7, typically at least about 1.9, and often at least about 2.1, and/or (iii) with respect to cyclooctane and ethylbenzene of generally at least about 1.6, typically at least about 1.7, and often at least about 1.8.

In representative embodiments, the desired relative volatility (a), competitive factor (D), and/or other favorable extractive distillation operating characteristics are obtained upon distilling the liquid mixture at sub-atmospheric pressure, for example at an absolute pressure of generally less than about 800 millibar, typically less than about 400 millibar, and often less than about 300 millibar, with an exemplary pressure ranges being from about 50 millibar to about 800 millibar, from about 100 millibar to about 400 millibar, and from about 150 to about 300 millibar.

A flowscheme corresponding to a representative extractive distillation zone 400 (as EB separation unit 400) is illustrated in FIG. 5. According to this embodiment, portion 2A/4A/6A/8A fed to extractive distillation zone 400 (which portion 2A may represent all of impure ethylbenzene-containing feed 2) and comprising both ethylbenzene and other $C_8$ aromatic compound(s) (e.g., ortho-xylene, meta-xylene, and/or para-xylene), in addition to one or more non-aromatic compounds (e.g., non-aromatic hydrocarbons such as isomers of trimethylcyclohexane and/or n-octane), is subjected to upstream distillation in non-aromatic removal column 445. A non-aromatic extractive agent (selective for extractive distillation of non-aromatic compounds, such as non-aromatic hydrocarbons) stream 410 may be combined with portion 2A/4A/6A/8A, either prior to or within non-aromatic removal column 445, to facilitate the desired removal of at least one of the non-aromatic compounds (e.g., non-aromatic hydrocarbons). As shown, an optional non-aromatic extractive agent compound make-up stream 412A may also be introduced, continuously or intermittently, to non-aromatic removal column 445, to replace any minor quantities of the non-aromatic extractive agent compound that are not recovered in recycle stream 422. An overhead removal fraction, as non-aromatic compound-enriched stream 401, enriched in the at least one non-aromatic compound and depleted in at least one $C_8$ aromatic compound, relative to portion 2A/4A/6A/8A, is withdrawn from non-aromatic removal column 445. This results in the removal of the at least one non-aromatic compound, which may have a boiling point comparable to, such as within 15° C. (+/−15° C. or +/−27° F.), within 10° C. (+/−10° C. or +/−18° F.), or possibly within 5° C. (+/−5° C. or +/−9° F.) of, the other $C_8$ aromatic compound(s) (e.g., ortho-xylene, meta-xylene, and/or para-xylene), present in portion 2A/4A/6A/8A. Non-aromatic removal column 445 may also serve to remove water from portion 2A/4A/6A/8A, for example to achieve a desirably low water content in pretreated bottoms fraction 414 and/or liquid mixture (LM). Alternatively, portion 2A/4A/6A/8A may be subjected to a separate, optional water removal step, upstream of non-aromatic removal column 445. The removal of water may be economically advantageous, insofar as the total material being subjected to extractive distillation is reduced, and consequently the associated energy requirements. Other advantages may also result, in terms of separation performance.

Pretreated bottoms fraction 414 is recovered from non-aromatic removal column 445 (i.e., from this upstream distillation), as a purified feed stream to the extractive distillation. This purified feed stream is enriched, relative to portion 2A/4A/6A/8A, in both ethylbenzene and the other $C_8$ aromatic compound(s), as well as optionally enriched in a non-aromatic extractive agent compound that is introduced to non-aromatic removal column 445 with non-aromatic extractive agent stream 410. Pretreated bottoms fraction 414 is likewise depleted, relative to portion 2A/4A/6A/8A, in one or more of the non-aromatic compounds present in this stream. Pretreated bottoms fraction 414 is then introduced into extractive distillation column 455 with a recycle portion 422B of recycle stream (or second bottoms fraction) 422 comprising an ethylbenzene extractive agent, or namely an extractive agent compound as described herein. Pretreated bottoms fraction 414 and recycle portion 422B may be combined either prior to or within extractive distillation column 455. Recycle portion 422B therefore can provide some or all (at least a portion) of the extractive agent compound fed to extractive distillation column 455. As shown, an optional extractive agent compound make-up stream 412B may also be introduced, continuously or intermittently, to extractive distillation column 455 to replace any minor quantities of the extractive agent compound that are not recovered in recycle stream 422.

In extractive distillation column 455, therefore, liquid mixture (LM) comprising pretreated bottoms fraction 414, and the extractive agent compound present in recycle portion 422B and optional make-up stream 412B, is distilled. This extractive distillation provides ethylbenzene-rich product 402 that, relative to pretreated bottoms fraction 414 and also relative to liquid mixture (LM), is enriched in ethylbenzene and depleted in both the extractive agent compound and at least one of the other $C_8$ aromatic compounds (e.g., one or more isomers of xylene) present in pretreated bottoms fraction 414. Extractive distillation column 455 also provides bottoms fraction 418 that, relative to pretreated bottoms fraction 414 and also relative to the liquid mixture (LM), is enriched in both the at least one of the other $C_8$ aromatic compounds and the extractive agent compound, and depleted in ethylbenzene. To purify and recover the extractive agent compound, bottoms fraction 418 is then introduced to, and distilled in, extractive agent recovery column 465 to provide second bottoms fraction 422 that, relative to bottoms fraction 418, is enriched in the extractive agent compound and optionally also enriched in the non-aromatic extractive agent compound. Second bottoms fraction 422, relative to bottoms fraction 418, is also depleted in the at least one of the other $C_8$ aromatic compounds. In this manner, at least a portion of second bottoms fraction 422 may then be recovered and recycled, as recycle portion 422B, to extractive distillation column 455, to advantageously conserve material resources, by providing at least a portion of the extractive agent compound in liquid mixture (LM). Optionally, at least a second portion of second bottoms fraction 422 may also be recycled, as non-aromatic extractive agent stream 422C, to non-aromatic removal column 445. According to some embodiments, second bottoms fraction 422, recycle portion 422B, and/or non-aromatic extractive agent stream 422C may be further purified (e.g., using a further distillation, adsorbent separation, extraction etc.) to remove contaminants from these extractive agent-containing streams, prior to introduction to their respective columns. Optionally, second bottoms fraction bleed stream 422A may be used to prevent an excessive accumulation of unwanted impurities in the recycle of extractive agents. According to the embodiment depicted in FIG. 4, all or a portion of second bottoms fraction bleed stream 422A (FIG. 5) may correspond to $C_9^+$ hydrocarbon-enriched heavy fraction 47, all or a portion of which may be combined with $C_9^+$ hydrocarbon stream, exiting xylene column 100 as a low-boiling fraction (e.g., bottoms fraction).

Distilling of bottoms fraction 418 in extractive agent recovery column 465 further provides (i) ethylbenzene-depleted feed 2B, (ii) ethylbenzene-depleted $C_8$ aromatic hydrocarbon stream 4B, (iii) ethylbenzene-, para-xylene-depleted effluent 6B, or (iv) ethylbenzene-depleted, xylene-equilibrated isomerate 8B, that is fed to the para-xylene process flow loop in the case of (i) and returned to the para-xylene process flow loop (e.g., combined with respective portions bypassing the extractive distillation, as described above) in the case of (ii), (iii), and (iv). For the sake of conciseness, this stream may generally be referred to as ethylbenzene-depleted stream 2B/4B/6B/8B, fed to or returned to the para-xylene process flow loop, following extractive distillation. This stream 2B/4B/6B/8B, relative to bottoms fraction 418, is enriched in the at least one other $C_8$ aromatic compound(s) (e.g., ortho-xylene, meta-xylene, and/or para-xylene) and depleted in the extractive agent compound and optionally also depleted in the non-aromatic extractive agent compound. The overall, extractive distillation zone 400 thereby advantageously provides ethylbenzene-rich product 402 that is purified in ethylbenzene, non-aromatic compound-enriched stream 401 that is purified in non-aromatic compounds, as well as ethylbenzene-depleted stream 2B/4B/6B/8B, as a further overhead fraction, that is enriched in the at least one other $C_8$ aromatic compound(s). Extractive distillation zone 400 thereby advantageously resolves these purified products while also providing recycle of the extractive agent compound. One or both of these purified products may be further purified (e.g., using a further distillation, adsorbent separation, extraction etc.) to achieve a higher purity level if desired.

According to the embodiment illustrated in FIG. 5, the extractive agent compound used in the upstream non-aromatic removal column 445, as well as in the extractive distillation column 455 (and in each case separated from the second bottoms fraction 422) may be the same compound. Alternatively, different extractive agent compounds may be used for these different purposes, in which case an optional separation (e.g., distillation) may be used to obtain the non-aromatic extractive agent stream 422C and the recycle portion 422B that are introduced to these respective columns. An exemplary non-aromatic extractive agent is acetonitrile. Preferably, however, the same compound may be used for both extractive distillations, leading to further advantages in terms of process simplification (e.g., fewer separation requirements) and associated cost reductions. As further illustrated in FIG. 5, total non-aromatic extractive agent input 410 to non-aromatic removal column 445 may be a combined amount of non-aromatic extractive agent compound make-up stream 412A and non-aromatic extractive agent stream 422C. Also, total ethylbenzene extractive agent input 416 to extractive distillation column 455 may be a combined amount of make-up stream 412B and recycle portion 422B.

Extractive Agent Compounds

For extractive agent compounds used in the processes described herein, and particularly in the extractive distillation zone 400 (as EB separation unit 400), the binding energy between such an extractive agent compound and ethylbenzene advantageously differs from the binding energy between the extractive agent compound and the at least one of the other (e.g., non-ethylbenzene) $C_8$ aromatic compounds, such as ortho-xylene, meta-xylene, or para-xylene. Binding energy is determined by a combination of several factors associated with the respective interacting compounds, including their polarity and steric effects. It now has been surprisingly discovered that extractive agent compounds having a carbocyclic (e.g., and also aromatic) or heterocyclic ring structure being substituted at substitutable ring positions with (i) at least one $NR^aR^b$ radical (i.e., $—NR^aR^b$ substituent), wherein $R^a$ and $R^b$ are independently selected from the group consisting of an oxygen radical, a hydrogen radical, and a hydrocarbyl radical having from about 1 to about 20 carbon atoms, and (ii) at least two halo radicals (i.e., halo substituents derived from their respective halogen atoms) are effective extractive agents for extractive distillation, such as for use in the separation of ethylbenzene from the at least one of the other $C_8$ aromatic compound aromatic compound(s) (e.g., ortho-xylene, meta-xylene, and/or para-xylene). While not being bound by theory, it is believed that the presence of both nitrogen and halogen atoms, together with the cyclic (e.g. aromatic) ring structure provide appropriate polarity, whereas the cyclic (e.g., aromatic) base structure itself provides important steric effects. As a result, extractive agent compounds comprising these features in combination can attractively interact with non-ethylbenzene $C_8$ aromatic compounds, but can repulsively interact with ethylbenzene, thereby facilitating the distillative separation of non-ethylbenzene $C_8$ aromatic compounds, particularly xylenes, and the extractive agent compound(s) in a bottoms fraction and ethylbenzene in an overhead fraction.

According to representative embodiments, the extractive agent compound is a compound according to Formula (I):

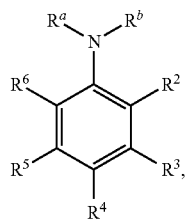

(I)

wherein $R^a$ and $R^b$ are each bonded to the nitrogen atom illustrated in this formula and are independently selected from the group consisting of an oxygen radical, a hydrogen radical, and a hydrocarbyl radical having from about 1 to about 20 carbon atoms. $R^a$ and $R^b$ are each bonded to the nitrogen atom shown in Formula (I) above via a single covalent bond, a double covalent bond, or a resonance stabilized covalent bond.

In the case of both $R^a$ and $R^b$ being an oxygen radical, the radical group $—NR^aR^b$ represents nitro ($—NO_2$), as a substituent of the benzene ring illustrated Formula (I), with nitro having a structure that can be represented as

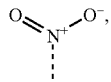

or alternatively represented with resonance stabilization as

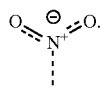

In the case of both $R^a$ and $R^b$ being hydrogen, the radical group $—NR^aR^b$ represents a primary amino group ($—NH_2$).

Otherwise, $R^a$ and $R^b$, together with the nitrogen atom shown in Formula (I) above to which they are commonly bonded, may form a 5- to 8-membered ring, wherein one or more ring members (e.g., carbon atom ring members) may be substituted. Suitable substituents of the ring members are those substituents identified below as substituents (1) or (2) of one or more carbon atoms of a hydrocarbyl radical. According to exemplary embodiments, $NR^aR^b$ may form a 5-membered ring substituent, such as pyrrolyl, dihydropyrrolyl, tetrahydropyrrolyl, or pyrrolidinyl, or alternatively may form a 6-membered ring substituent, such as pyridinyl, dihydropyridinyl, tetrahydropyridinyl, or piperidinyl.

In formula (I) above, $R^2$-$R^6$ are substituents of the benzene ring illustrated in this formula (other than the substituent, $NR^aR^b$) and are independently selected from the group consisting of halo, a hydrogen radical, and a hydrocarbyl radical having from about 1 to about 20 carbon atoms. Preferably, at least two of $R^2$-$R^6$ are halo, as in the case of such at least two of $R^2$-$R^6$ being chloro. For example, $R^3$ and $R^4$ may both be halo, such as chloro. Alternatively, $R^2$ and $R^3$ may both be halo, such as chloro.

In the case of one or more of $R^a$, $R^b$, $R^2$, $R^3$, $R^4$, $R^5$, or $R^6$ being a hydrocarbyl radical having from about 1 to about 20 carbon atoms, such a hydrocarbyl radical refers namely to a saturated or partially unsaturated straight chain, branched, or cyclic radical of a hydrocarbon, in which one or more carbon atoms in such hydrocarbyl radical are optionally substituted and/or replaced, for example substituted according to (1) and/or (2) below, or replaced according to (3) below. In particular, in representative hydrocarbyl radicals having from about 1 to about 20 carbon atoms, (1) one or more carbon atoms having one or more bound hydrogen atoms (i.e., hydrogen radicals) are optionally substituted with a monovalent radical independently selected from alkyl, alkenyl, alkynyl, cycloalkyl, heterocycloalkyl, aryl, heteroaryl, $—OH$, $—SH$, $—SOH$, $—SO_2H$, $—SO_3H$, $—NH_2$, $—NO_2$, $—CO_2H$, $—CONH_2$, $—CN$, $—F$, $—Cl$, $—Br$, and $—I$, wherein the monovalent heteroatomic radicals $—OH$, $—SH$, $—SOH$, $—SO_2H$, $—SO_3H$, $—NH_2$, $—CO_2H$, $—CONH_2$ optionally have one or more bound hydrogen atoms independently replaced by alkyl, alkenyl, alkynyl, cycloalkyl, heterocycloalkyl, aryl, heteroaryl, $—OH$, $—SH$, $—SOH$, $—SO_2H$, $—SO_3H$, $—NH_2$, $—NO_2$, $—CO_2H$, $—CONH_2$, $—CN$, $—F$, $—Cl$, $—Br$, or $—I$;

(2) one or more carbon atoms having two or more bound hydrogen atoms are optionally substituted with a divalent radical independently selected from $=O$, $=S$, $=NH$, =NOH, and =NNH$_2$, wherein the divalent heteroatomic radicals =NH, =NOH, and =NNH$_2$ optionally have one or more bound hydrogen atoms (i.e., hydrogen radicals) independently replaced by alkyl, alkenyl, alkynyl, cycloalkyl, heterocycloalkyl, aryl, heteroaryl, —OH, —SH, —SOH, —SO$_2$H, —SO$_3$H, —NH$_2$, —NO$_2$, —CO$_2$H, —CONH$_2$, —CN, —F, —Cl, —Br, or —I; and (3) one or more methylene carbon atoms (—CH$_2$—) are optionally replaced by a divalent radical independently selected from alkyl, alkenyl, alkynyl, cycloalkyl, heterocycloalkyl, aryl, heteroaryl, —O—, —S—, —NH—, —OCO—, —CO$_2$—, —CONH—, —OCONH—, and —CO$_2$NH—, wherein the divalent heteroatomic radicals —NH—, —CONH—, —OCONH—, and —CO$_2$NH— optionally have one or more hydrogen radicals independently replaced by alkyl, alkenyl, alkynyl, cycloalkyl, heterocycloalkyl, aryl, heteroaryl, —OH, —SH, —SOH, —SO$_2$H, —SO$_3$H, —NH$_2$, —NO$_2$, —CO$_2$H, —CONH$_2$, —CN, —F, —Cl, —Br, or —I.

According to other embodiments, one or both of $R^a$ and $R^b$, and/or one or more of $R^2$, $R^3$, $R^4$, $R^5$, or $R^6$ (e.g., those substituents $R^2$, $R^3$, $R^4$, $R^5$, or $R^6$ that are not halo) may otherwise be independently selected from, in addition to a hydrogen radical or hydrocarbyl radical having from about 1 to about 20 carbon atoms as defined above, a monovalent heteroatomic radical such as —OH, —SH, —SOH, —SO$_2$H, —SO$_3$H, —NH$_2$, —NO$_2$, —CO$_2$H, —CONH$_2$, and —CN, wherein the monovalent heteroatomic radicals —OH, —SH, —SOH, —SO$_2$H, —SO$_3$H, —NH$_2$, —CO$_2$H and —CONH$_2$ optionally have one or more hydrogen radicals independently replaced by alkyl, alkenyl, alkynyl, cycloalkyl, heterocycloalkyl, aryl, heteroaryl, —OH, —SH, —SOH, —SO$_2$H, —SO$_3$H, —NH$_2$, —NO$_2$, —CO$_2$H, —CONH$_2$, —CN, —F, —Cl, —Br, or —I.

A representative hydrocarbyl radical having from about 1 to about 20 carbon atoms may be a saturated or partially unsaturated straight chain, branched, or cyclic radical of a hydrocarbon, optionally in which no carbon atom is substituted according to (1) above, or in which no carbon atom is substituted according to (2) above, or in which no carbon atom is replaced according to (3) above. In the case of a saturated cyclic radical of a hydrocarbon, a representative hydrocarbyl radical may be cycloalkyl (e.g., cyclopentyl or cyclohexyl). In the case of a partially unsaturated cyclic radical of a hydrocarbon, a representative hydrocarbyl radical may be aryl (e.g., cyclopentadienyl or phenyl).

A representative hydrocarbyl radical having from about 1 to about 20 carbon atoms may be a saturated straight chain, branched, or cyclic radical of an aliphatic hydrocarbon, optionally in which no carbon atom is substituted according to (1) above, or in which no carbon atom is substituted according to (2) above, or in which no carbon atom is replaced according to (3) above.

A representative hydrocarbyl radical having from about 1 to about 20 carbon atoms may be selected from the group consisting of alkyl, alkenyl, alkynyl, cycloalkyl, heterocycloalkyl, aryl, heteroaryl, (cycloalkyl)alkyl, (heterocycloalkyl)alkyl, aralkyl, heteroaralkyl, hydroxy, alkoxy, cycloalkoxy, aryloxy, hydroxycarbonyl, hydroxycarbonylalkyl, alkanoyl, alkanoyloxy, alkoxycarbonyl, thiol, alkylthiol, amino, halo, haloalkyl, amido, alkylamido, (cycloalkyl)amido, (heterocycloalkyl)amido, arylamido, and (heteroaryl)amido.

A representative hydrocarbyl radical having from about 1 to about 20 carbon atoms may be alkyl, such as $C_1$-$C_4$ alkyl (e.g., methyl, ethyl, propyl, and butyl).

According to other embodiments, one or both of $R^a$ and $R^b$, and/or one or more of $R^2$, $R^3$, $R^4$, $R^5$, or $R^6$ (e.g., those substituents $R^2$, $R^3$, $R^4$, $R^5$, or $R^6$ that are not halo), for example both of $R^a$ and $R^b$, and/or all of $R^2$, $R^3$, $R^4$, $R^5$, or $R^6$ that are not halo, are hydrogen radicals.

According to specific embodiments, the aromatic compound of the extractive agent may be an isomer of dichloronitrobenzene, for example a compound in which $NR^aR^b$ represents nitro (NO$_2$), two of the substituents $R^2$, $R^3$, $R^4$, $R^5$, and $R^6$ represent chloro, and the remaining substituents $R^2$, $R^3$, $R^4$, $R^5$, and $R^6$ represent hydrogen. In the particular case in which $NR^aR^b$ represents nitro (NO$_2$); $R^3$ and $R^4$ represent chloro; and $R^2$, $R^5$, and $R^6$ represent hydrogen, the aromatic compound of the extractive agent is 1,2-dichloro-4-nitrobenzene. In the particular case in which $NR^aR^b$ represents nitro (NO$_2$); $R^2$ and $R^3$ represent chloro; and $R^3$, $R^5$, and $R^6$ represent hydrogen, the aromatic compound of the extractive agent is 1,2-dichloro-3-nitrobenzene. The compounds 1,2-dichloro-4-nitrobenzene and 1,2-dichloro-3-nitrobenzene have the following structures:

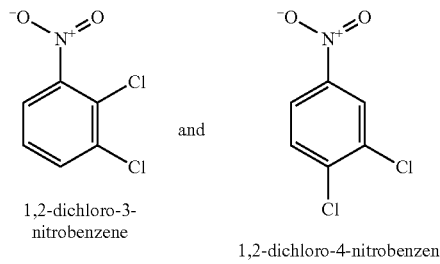

1,2-dichloro-3-nitrobenzene 1,2-dichloro-4-nitrobenzene

According to other specific embodiments, the aromatic compound of the extractive agent may be an isomer of dichloroaniline, for example a compound in which $NR^aR^b$ represents amino (NH$_2$), two of the substituents $R^2$, $R^3$, $R^4$, $R^5$, and $R^6$ represent chloro, and the remaining substituents $R^2$, $R^3$, $R^4$, $R^5$, and $R^6$ represent hydrogen. In the particular case in which $NR^aR^b$ represents amino (NH$_2$); $R^3$ and $R^4$ represent chloro; and $R^2$, $R^5$, and $R^6$ represent hydrogen, the aromatic compound of the extractive agent is 3,4-dichloroaniline. This compound has the following structure:

3,4 dichloroaniline

Mixtures of any two or more extractive agent compounds, such as two or more compounds according to Formula (I) above, may also be used, for example in a liquid mixture (LM) of an extractive distillation process described above. According to particular embodiments, a mixture of an isomer of dichloroaniline and an isomer of dichloronitrobenzene, such as a mixture of (i) 3,4-dichloroaniline and (ii) 1,2-dichloro-4-nitrobenzene or 1,2-dichloro-3-nitrobenzene, at any mixing ratio (e.g., 5/95 w/w of (i):(ii), 25/75 w/w of (i):(ii), 50/50 w/w of (i):(ii), 75/25 w/w of (i):(ii), or 95/5 w/w of (i):(ii)) may be used.

For purposes of the present invention, and consistent with accepted chemical nomenclature for radicals such as substituent groups, "Halo," alone or in combination, represents a halogen radical selected from fluoro, chloro, bromo, and iodo (i.e., —F, —Cl, —Br, and —I, respectively). According to preferred embodiments, "halo" represents fluoro or chloro, and more preferably represents chloro.

"Alkyl," as used alone or in combination with other radicals (i.e., alone or in combination), represents a straight or branched chain saturated hydrocarbon radical, which may be bonded at one end of the chain (e.g., as in a methyl group, —$CH_3$) or at two ends of the chain (e.g., as in a methylene group —$CH_2$—). Unless otherwise indicated, alkyl contains from 1 to 10 carbon atoms. "Alkenyl," alone or in combination, represents alkyl that contains one or more carbon-to-carbon double bonds. "Alkynyl," alone or in combination, represents alkyl that contains one or more carbon-to-carbon triple bonds.

"Cycloalkyl," alone or in combination, represents a monocyclic, bridged monocyclic, bicyclic, tricyclic or spiro ring saturated hydrocarbon radical, which may be bonded to a parent molecule at one or more (e.g., one or two) bonding sites, wherein each ring contains from 3 to 8 carbon atoms. "Heterocycloalkyl," alone or in combination, represents cycloalkyl having one or more carbon atoms replaced by an oxygen, nitrogen, or sulfur (including sulfoxide and sulfone), or otherwise replaced by a divalent radical having such heteroatom, such as =NH, =NOH, =$NNH_2$, =SO and =$SO_2$. "Aryl," alone or in combination, represents an unsaturated or partially unsaturated monocyclic, bridged monocyclic, bicyclic, tricyclic or spiro ring hydrocarbon radical, which may be bonded to a parent molecule at one or more (e.g., one or two) bonding sites, wherein each ring contains from 3 to 8 carbon atoms. "Heteroaryl," alone or in combination, represents aryl having one or more carbon atoms replaced by an oxygen, nitrogen, or sulfur heteroatom, or otherwise replaced by a divalent radical having such heteroatom, such as =NH, =NOH, =$NNH_2$, =SO, and =$SO_2$. Unless otherwise indicated or apparent from the name of a specific cycloalkyl, heterocycloalkyl, aryl, or heteroaryl radical, these cyclic radicals may be bonded in the molecules described herein at any ring positions available for bonding (i.e., at any substitutable ring position).

"Aralkyl," alone or in combination, represents alkyl in which a hydrogen atom is replaced by aryl. "Aralkenyl," alone or in combination, represents alkenyl in which a hydrogen atom is replaced by aryl. "Aralkynyl," alone or in combination, represents alkynyl in which a hydrogen atom is replaced by aryl. "Heteroaralkyl," "heteroaralkenyl," and "heteroaralkynyl," alone or in combination, represent alkyl, alkenyl, and alkynyl, respectively, in which a hydrogen atom is replaced by heteroaryl.

"Hydroxy," alone or in combination, represents the radical —OH. "Alkoxy," "alkenoxy," and "alkynyloxy," alone or in combination, represent alkyl, alkenyl, and alkynyl, respectively, that are bonded to a molecule through an —O— linkage. For example, alkoxy, alone or in combination, represents the radical alkyl-O—. "Cycloalkoxy," "heterocycloalkoxy," "aryloxy," and "heteroaryloxy," alone or in combination, represent cycloalkyl, heterocycloalkyl, aryl, and heteroaryl, respectively, that are bonded to a molecule through an —O— linkage.

"Carbonyl," alone or in combination, represents the radical —(C=O)—. "Thiocarbonyl," alone or in combination, represents the radical —(C=S)—. "Hydroxycarbonyl," alone or in combination, represents a radical of formic acid, —(C=O)—OH. "Alkanoyl," "alkenoyl," "alkynoyl," alone or in combination, represent alkyl, alkenyl, and alkynyl, respectively, that are bonded to a molecule through a carbonyl linkage. For example, alkanoyl, alone or in combination, represents the radical alkyl-(C=O)—. "Cycloalkanoyl," "heterocycloalkanoyl," "aroyl," and "heteroaroyl," alone or in combination, represent cycloalkyl, heterocycloalkyl, aryl, and heteroaryl, respectively, that are bonded to a molecule through a carbonyl linkage.

"Carbonyloxy," alone or in combination, represent carbonyl that is bonded to a molecule through an —O— linkage. "Alkanoyloxy," "alkenoyloxy," "alkynoyloxy," "cycloalkanoyloxy," "heterocycloalkanoyloxy," "aroyloxy," and "heteroaroyloxy," alone or in combination, represent alkanoyl, alkenoyl, alkynoyl, cycloalkanoyl, heterocycloalkanoyl, aroyl, and heteroaroyl, respectively, that are bonded to a molecule through an —O— linkage. For example, alkanoyloxy represents the radical alkyl-C(=O)—O—.

"Thiol," alone or in combination, represents an —S— or —SH linkage. "Alkylthiol," "alkenylthiol," and "alkynylthiol," alone or in combination, represent alkyl, alkenyl, and alkynyl, respectively, that are bonded to a molecule through an —S— linkage. For example, alkylthiol represents the radical alkyl-S—. "Thiolalkyl," "thiolalkenyl," and "thiolalkynyl," alone or in combination, represent radicals of the formula HS-alkyl-, HS-alkenyl-, and HS-alkynyl-, respectively.

"Amino," alone or in combination, embraces radicals of both primary (—$NH_2$) and secondary (—NH—) amines. Unless otherwise indicated, both primary amino and secondary amino radicals may be substituted at a hydrogen, or at both hydrogens in the case of primary amino, with one or two radicals independently selected from the group consisting of alkyl, alkenyl, alkynyl, cycloalkyl, aryl, and heteroaryl. "Alkylamino," "alkenylamino," and "alkynylamino," alone or in combination, represent alkyl, alkenyl, and alkynyl, respectively, that are bonded to a molecule through a secondary amino (—NH—) linkage. "Amido," alone or in combination, represent a carbonylamino radical —(C=O)—NH—. "Alkylamido," "alkenylamido," and "alkynylamido," alone or in combination, represent alkyl, alkenyl, and alkynyl, respectively, that are bonded to a molecule through an amido linkage. For example, alkylamido refers to the radical alkyl-(C=O)—NH—. "Imino," alone or in combination, represents the radical —(C=NH)—, wherein, unless otherwise indicated, imino may be substituted at a hydrogen with a radical as defined above with respect to amino.

"Heteroatom(s)," "heteroatomic group(s)," and "heteroatomic radical(s)" represent atoms of oxygen, nitrogen, and sulfur, as well as groups and radicals having these heteroatoms, such as =O, =S, =NH, =NOH, and =$NNH_2$.

The following examples are set forth as representative of the present invention. These examples are not to be construed as limiting the scope of the invention as other equivalent embodiments will be apparent in view of the present disclosure and appended claims.

Example 1

Using process simulation, the economics of para-xylene production in a conventional aromatics complex were compared to those utilizing integration with extractive distillation, and in particular utilizing distillation with an extractive agent compound as described above, for separation of ethylbenzene from the process flow loop. The comparison was based on this separation occurring between the para-xylene separation zone and xylene isomerization zone, as illustrated in FIG. 2. In addition to accounting for the upstream reformate splitter operation, the steps of xylene column distillation, para-xylene separation, and isomerization, as described above, were simulated. To improve the applicability of the simulations to commercial processes, the operation of a $C_7$ (toluene)/$C_9$ transalkylation (disproportionation) unit was also included in the modeling. Para-xylene separation in each case was based on crystallization.

Three separate cases were identified and analyzed. The first case, identified as "Conventional," did not utilize extractive distillation, but instead was modeled on the basis of using a conventional isomerization catalyst, having ethylbenzene dealkylation activity, for limiting the accumulation of ethylbenzene in the process flow loop. The second case, identified as "EB-X 18%," was modeled on the basis of the para-xylene-depleted effluent from the para-xylene separation zone, and consequently the feed to the extractive distillation column, containing 18 wt-% ethylbenzene. The third case, identified as "EB-X 25%," was modeled on the basis of these streams containing 25 wt-% ethylbenzene. Because of the higher concentration of ethylbenzene in the process flow loop, only 6 wt-% of the para-xylene-depleted effluent was needed for extractive distillation in the third case, compared to 9 wt-% in the second case. The simulation therefore illustrated an expected tradeoff that would be realized between the concentration of ethylbenzene being recycled and the proportion of the recycle loop being fed to the extractive distillation. In both cases EB-X 18% and EB-X 25%, the requirement for ethylbenzene conversion over the isomerization catalyst was removed and corresponding, milder operating conditions were used in the isomerization reactor simulation, including liquid phase operation without the addition of hydrogen.

Based on the process simulation studies, the estimated investment costs for the "Conventional," "EB-X 18%," and "EB-X 25%" cases were comparable. Whereas the latter two cases required additional capital associated with implementing extractive distillation, it was found that this could be offset by reductions in expenditure due to decreased capacity of other process operations, most notably an approximately 50% reduction in expenditure for isomerization.

In considering total operating costs (including utilities), with respect to the cases modeled based on an extractive distillation step, an important savings resulted from the calculated hydrogen consumption being only about 40% of that for the "Traditional" case, due to the absence of hydrogen added to the isomerization zone. Moreover, in terms of product yields and associated product stream values, simulation of the isomerization reaction occurring in the liquid phase, according to the second and third cases, resulted in a significantly lower, estimated aromatic ring loss, compared to vapor phase isomerization in the "Traditional" case. Other advantages, according to the process models, of operating with extractive distillation according to the EB-X 18% and EB-X 25% cases, included an increase in the total liquid product for the aromatics complex of >2% and a decrease in the off gas make of >15%. Moreover, about 6.5 wt-% of the total liquid product in the EB-X 18% and EB-X 25% cases was recovered as high purity ethylbenzene, suitable for styrene monomer production. No such revenue-generating steam was associated with the "Traditional" case, consistent with current commercial para-xylene production facilities.

For the cases of the modeled complexes generating approximately 309,000 kg/hr (2.6 million metric tons/year) of para-xylene, the operational benefits (added product credit minus added operating costs) of adding the extractive distillation of ethylbenzene, according to the EB-X 18% and EB-X 25% cases, were determined to be 70-80 million dollars/year, relative to the "Traditional" case, assuming a crude oil price of approximately $50/barrel.

Overall aspects of the invention relate to processes for producing para-xylene, utilizing the steps of distillation to separate a $C_8$ aromatic hydrocarbon stream, followed by separating a para-xylene rich product from this steam and isomerizing the residual para-xylene-depleted effluent to generate additional amount of para-xylene. By forming a recycle loop, back to the distillation and/or downstream separation of the para-xylene rich product, such additional amount can also be recovered. Advantageously, the use of extractive distillation or other separation to remove ethylbenzene and optionally other co-boiling compounds (e.g., $C_9$ non-aromatic hydrocarbons) can improve process economics insofar as the conventional requirements for ethylbenzene conversion in the isomerization zone can be mitigated and a purified ethylbenzene product can be generated.

Those having skill in the art, with the knowledge gained from the present disclosure, will recognize that various changes could be made in these processes without departing from the scope of the present invention. Mechanisms used to explain theoretical or observed phenomena or results, shall be interpreted as illustrative only and not limiting in any way the scope of the appended claims.

The invention claimed is:

1. A process for producing para-xylene, the process comprising:
    separating, in a xylene column, a $C_8$ aromatic hydrocarbon stream and a $C_9^+$ hydrocarbon stream, from at least a portion of an impure ethylbenzene-containing feed;
    separating, in a xylene separation zone, a para-xylene rich product from at least a portion of the $C_8$ aromatic hydrocarbon stream, to provide a para-xylene-depleted effluent;
    isomerizing, in an isomerization zone, at least a portion of the para-xylene-depleted effluent, to provide a xylene-equilibrated isomerate;
    recycling at least a portion of the xylene-equilibrated isomerate to the xylene column, and
    separating, in an ethylbenzene (EB) separation unit, an ethylbenzene-rich product from (i) a portion of the ethylbenzene-containing feed to provide an ethylbenzene-depleted feed, and combining at least a portion of the ethylbenzene-depleted feed with all or a portion of the $C_8$ aromatic hydrocarbon stream, (ii) a portion of the $C_8$ aromatic hydrocarbon stream to provide an ethylbenzene-depleted $C_8$ aromatic hydrocarbon stream, and combining at least a portion of the ethylbenzene-depleted $C_8$ aromatic hydrocarbon stream with a portion of the $C_8$ aromatic hydrocarbon stream bypassing the EB separation unit, (iii) a portion of the para-xylene-depleted effluent to provide an ethylbenzene-, para-xylene-depleted effluent, and combining at least a portion of the ethylbenzene-, para-xylene-depleted effluent with a portion of the para-xylene-depleted effluent bypassing the EB separation unit, (iv) a portion of the xylene-equilibrated isomerate to provide an ethylbenzene-depleted, xylene-equilibrated isomerate, and combining at least a portion of the ethylbenzene-depleted, xylene-equilibrated isomerate with a portion of the xylene-equilibrated isomerate bypassing the EB separation unit, or a combination thereof.

2. The process of claim 1, wherein the ethylbenzene-rich product is separated from a portion of the para-xylene-depleted effluent to provide the ethylbenzene, para-xylene-depleted effluent.

3. The process of claim 1, wherein the ethylbenzene-containing feed comprises a product of naphtha reforming, naphtha cracking, or transalkylation.

4. The process of claim 3, wherein the product of naphtha cracking is pyrolysis gasoline.

5. The process of claim 1, wherein the xylene separation zone comprises adsorptive separation or crystallization for the separating of the para-xylene rich product.

6. The process of claim 1, wherein the isomerization zone comprises an isomerization reactor, through which the at least a portion of the para-xylene-depleted effluent is passed in the liquid phase.

7. The process of claim 6, wherein the isomerization reactor is operated under isomerization conditions including a temperature from about 200° C. (392° F.) to about 300° C. (572° F.) and an absolute pressure from about 2.5 MPa (363 psi) to about 4.5 MPa (653 psi).

8. The process of claim 1, wherein a para-xylene process flow loop is completed by said recycling of said at least a portion of the xylene-equilibrated isomerate to the xylene column.

9. The process of claim 1, wherein the EB separation unit comprises extractive distillation.

10. A process for producing para-xylene, the process comprising forming a para-xylene process flow loop comprising: (i) a $C_8$ aromatic hydrocarbon stream, separated as a low-boiling fraction in a xylene column, (ii) a para-xylene-depleted effluent, separated in a xylene separation zone from at least a portion of the $C_8$ aromatic hydrocarbon stream, and (iii) a xylene-equilibrated isomerate, provided from isomerization of at least a portion of the para-xylene-depleted effluent,
wherein the process flow loop is completed by recycling at least a portion of the xylene-equilibrated isomerate to the xylene column, and
wherein an overall conversion of ethylbenzene introduced into the para-xylene process flow loop is less than about 20 wt-%, or wherein an overall loss of aromatic rings introduced into the para-xylene process flow loop is less than about 5 mol-%,
the process further comprising removing an ethylbenzene-rich product, comprising ethylbenzene in an amount of greater than about 90 wt-%, from the para-xylene-depleted effluent of the para-xylene process flow loop or from the xylene-equilibrated isomerate of the para-xylene process flow loop,
wherein the removing of the ethylbenzene-rich product is performed by extractive distillation.

11. The process of claim 10, wherein greater than about 80 wt-% of the ethylbenzene introduced into the para-xylene process flow loop is present in an ethylbenzene-containing feed to the xylene column and/or to an ethylbenzene (EB) separation unit.

12. The process of claim 10, wherein the isomerization of the at least a portion of the para-xylene-depleted effluent is carried out with a per-pass aromatic ring loss of less than about 2 mol-%.

13. The process of claim 10, wherein each of (i), (ii), and (iii) of the process flow loop comprises less than about 25 wt-% ethylbenzene.

14. The process of claim 10, wherein the ethylbenzene-rich product comprises greater than about 95 wt-% ethylbenzene.

15. The process of claim 14, wherein the ethylbenzene-rich product comprises greater than about 99.5 wt-% ethylbenzene.

16. A process for producing para-xylene, the process comprising:
separating an ethylbenzene-rich product from a portion of an ethylbenzene-containing feed to provide an ethylbenzene-depleted feed;
separating, in a xylene column, a $C_8$ aromatic hydrocarbon stream as low-boiling fraction and a $C_9^+$ hydrocarbon stream as a high-boiling fraction, from a portion of the ethylbenzene-containing feed;
combining at least a portion of the ethylbenzene-depleted feed with a $C_8$ aromatic hydrocarbon stream, to provide a combined, ethylbenzene-depleted feed/$C_8$ aromatic hydrocarbon stream;
in a xylene separation zone, separating a para-xylene rich product from at least a portion of the combined, ethylbenzene-depleted feed/$C_8$ aromatic hydrocarbon stream, to provide a para-xylene-depleted effluent;
in an isomerization zone, isomerizing at least a portion of the para-xylene-depleted effluent, to provide a xylene-equilibrated isomerate; and
recycling at least a portion of the xylene-equilibrated isomerate to the xylene column,
wherein a per-pass ethylbenzene conversion in the isomerization zone is less than about 5 wt-%.

17. The process of claim 16, wherein the separating of the ethylbenzene-rich product is performed by extractive distillation.

18. The process of claim 17, wherein the extractive distillation further provides a $C_9^+$ hydrocarbon-enriched heavy fraction, the process further comprising combining the $C_9^+$ hydrocarbon-enriched heavy fraction with the $C_9^+$ hydrocarbon stream, separated from the xylene column.

19. The process of claim 1, wherein (i) the ethylbenzene-containing feed or portion thereof, (ii) the portion of the $C_8$ aromatic hydrocarbon stream, (iii) the portion of the para-xylene-depleted effluent, or (iv) the portion of the xylene-equilibrated isomerate, from which the ethylbenzene-rich product is separated, represents from about 1 wt-% to about 95 wt-% of the para-xylene-depleted effluent, or the xylene-equilibrated isomerate.

20. The process of claim 1, wherein (i) the ethylbenzene-containing feed or portion thereof, (ii) the portion of the $C_8$ aromatic hydrocarbon stream, (iii) the portion of the para-xylene-depleted effluent, or (iv) the portion of the xylene-equilibrated isomerate, from which the ethylbenzene-rich product is separated, comprises from about 3 wt-% to about 50 wt-% of ethylbenzene.

* * * * *